United States Patent [19]
Robertson et al.

[11] Patent Number: 5,984,959
[45] Date of Patent: Nov. 16, 1999

[54] HEART VALVE REPLACEMENT TOOLS AND PROCEDURES

[75] Inventors: John Charles Robertson, Bloomfield; Brian W. Moulder; Roberto Pedros, both of Seymour, all of Conn.

[73] Assignee: United States Surgical, Norwalk, Conn.

[21] Appl. No.: 08/932,570

[22] Filed: Sep. 19, 1997

[51] Int. Cl.⁶ .................................................... A61F 2/24
[52] U.S. Cl. .................................................. 623/2
[58] Field of Search ..................... 623/2, 900; 294/94, 294/96, 100

[56] References Cited

U.S. PATENT DOCUMENTS

| | | |
|---|---|---|
| Re. 34,150 | 12/1992 | Santilli et al. . |
| 2,682,057 | 6/1954 | Lord . |
| 3,143,742 | 8/1964 | Cromie . |
| 3,371,352 | 3/1968 | Siposs et al. . |
| 3,464,065 | 9/1969 | Cromie . |
| 3,508,281 | 4/1970 | Cromie . |
| 3,524,202 | 8/1970 | Cromie . |
| 3,546,710 | 12/1970 | Shumakov et al. . |
| 3,574,865 | 4/1971 | Hamaker . |
| 3,587,115 | 6/1971 | Shiley . |

(List continued on next page.)

FOREIGN PATENT DOCUMENTS

| | | |
|---|---|---|
| 809965 | 4/1969 | Canada . |
| 0103546 | 3/1984 | European Pat. Off. . |
| 0200419 | 11/1986 | European Pat. Off. . |
| 207339 | 7/1968 | U.S.S.R. . |
| 782808 | 11/1980 | U.S.S.R. . |
| 878285 | 11/1981 | U.S.S.R. . |
| 969265 | 10/1982 | U.S.S.R. . |
| 1008937 | 7/1984 | U.S.S.R. . |
| 1507368 | 9/1989 | U.S.S.R. . |
| 1621912 | 1/1991 | U.S.S.R. . |
| 1690738 | 11/1991 | U.S.S.R. . |
| 1697790 | 12/1991 | U.S.S.R. . |
| 87/05489 | 9/1987 | WIPO . |
| 91/01697 | 2/1991 | WIPO . |
| 91/17720 | 11/1991 | WIPO . |
| 93/01768 | 2/1993 | WIPO . |
| 94/01062 | 1/1994 | WIPO . |
| 94/18909 | 9/1994 | WIPO . |

OTHER PUBLICATIONS

The Journal of Thoracic and Cardiovascular Surgery, vol. 52, No. 4, Oct. 1966, p. 41.
The Journal of Thoracic and Cardiovascular Surgery, George J. Magovern, M.D. et al., vol. 48, No. 3, Sep. 1964, pp. 346–361.
The Journal of Thoracic And Cardiovascular Surgery, G.J. Magovern, M.D. et al., vol. 46, Dec. 1963, No. 6, pp. 726–736.
The Journal of Thoracic And Cardiovascular Surgery, vol. 57, No. 3, Advertising p. 31, Mar. 1969.
The Journal of Thoracic and Cardiovascular Surgery, G.J. Magovern, M.D. et al., vol. 59, No. 1, Jan. 1970, pp. 109–116.
The Bulletin of the Dow Corning Center for Aid to Medical Research, vol. 6, No. 2, Apr. 1964, pp. 5–8.

*Primary Examiner*—David H. Willse

[57] ABSTRACT

There are disclosed various systems for installing a heart valve within a patient. In a first system, there are provided a heart valve installation assembly and an expandable heart valve ring installation assembly, each of which comprises a separate tool. The expandable heart valve ring assembly is provided to position and expand a heart valve ring into engagement with tissue. The valve installation assembly is provided to position and engage the heart valve with the expandable heart valve ring. In a second system, the heart valve installation assemblies and expandable ring installation assemblies are provided on a single tool or instrument. There are also disclosed various methods of installing an expandable heart valve ring within a heart and positioning and installing an artificial synthetic heart valve within the expanded heart valve ring.

23 Claims, 21 Drawing Sheets

U.S. PATENT DOCUMENTS

| | | |
|---|---|---|
| 3,691,567 | 9/1972 | Cromie . |
| 3,722,004 | 3/1973 | Cromie . |
| 3,828,787 | 8/1974 | Anderson et al. . |
| 3,996,623 | 12/1976 | Kaster . |
| 4,056,854 | 11/1977 | Boretos et al. . |
| 4,233,690 | 11/1980 | Akins . |
| 4,506,394 | 3/1985 | Bédard . |
| 4,535,483 | 8/1985 | Klawitter et al. . |
| 4,585,453 | 4/1986 | Martin et al. . |
| 4,602,911 | 7/1986 | Ahmadi et al. . |
| 4,683,883 | 8/1987 | Martin . |
| 4,865,600 | 9/1989 | Carpentier et al. . |
| 4,932,965 | 6/1990 | Phillips . |
| 4,960,424 | 10/1990 | Grooters . |
| 5,041,130 | 8/1991 | Cosgrove et al. . |
| 5,074,858 | 12/1991 | Ramos Martinez . |
| 5,089,015 | 2/1992 | Ross . |
| 5,167,223 | 12/1992 | Koros et al. . |
| 5,197,979 | 3/1993 | Quintero et al. . |
| 5,236,450 | 8/1993 | Scott . |
| 5,290,300 | 3/1994 | Cosgrove et al. . |
| 5,326,373 | 7/1994 | Nagase . |
| 5,350,420 | 9/1994 | Cosgrove et al. . |
| 5,370,685 | 12/1994 | Stevens . |
| 5,403,305 | 4/1995 | Sauter et al. . |
| 5,423,851 | 6/1995 | Samuels . |
| 5,476,510 | 12/1995 | Eberhardt et al. . |
| 5,480,425 | 1/1996 | Ogilive . |
| 5,500,016 | 3/1996 | Fisher . |
| 5,509,930 | 4/1996 | Love . |
| 5,522,884 | 6/1996 | Wright . |
| 5,522,885 | 6/1996 | Love et al. . |
| 5,531,785 | 7/1996 | Love et al. . |
| 5,545,209 | 8/1996 | Roberts et al. . |
| 5,545,214 | 8/1996 | Stevens . |
| 5,571,170 | 11/1996 | Palmaz et al. . |
| 5,571,215 | 11/1996 | Sterman et al. . |
| 5,578,076 | 11/1996 | Krueger et al. . |
| 5,582,607 | 12/1996 | Lackman . |
| 5,584,879 | 12/1996 | Reimold et al. . |
| 5,593,435 | 1/1997 | Carpentier et al. . |
| 5,713,951 | 2/1998 | Garrison et al. . |
| 5,716,370 | 2/1998 | Williamson, IV et al. . |
| 5,716,398 | 2/1998 | Sparks et al. . |
| 5,716,401 | 2/1998 | Eberhardt et al. . |
| 5,716,402 | 2/1998 | Reif . |

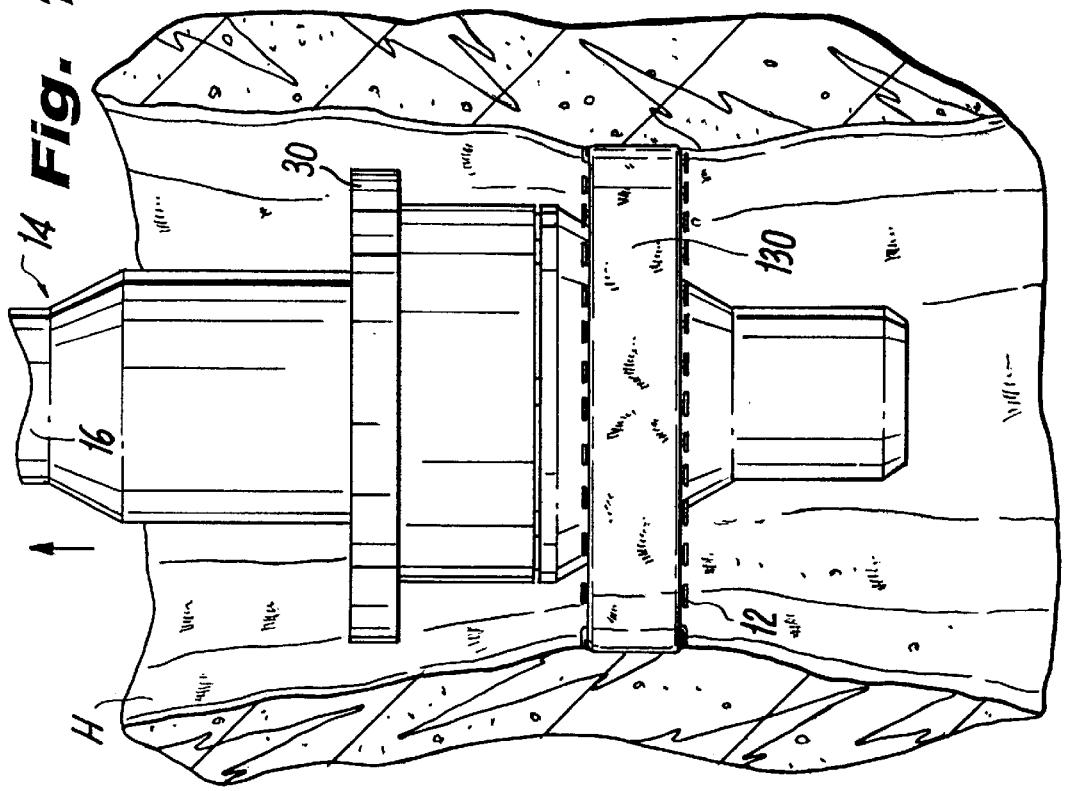
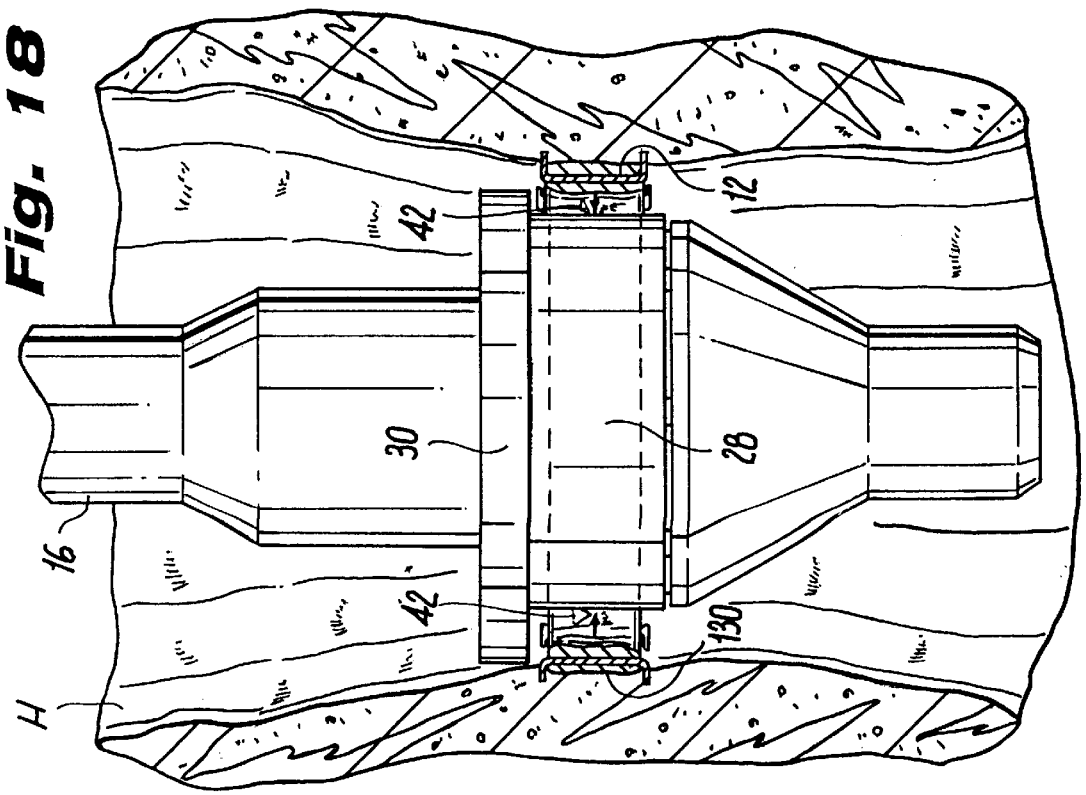

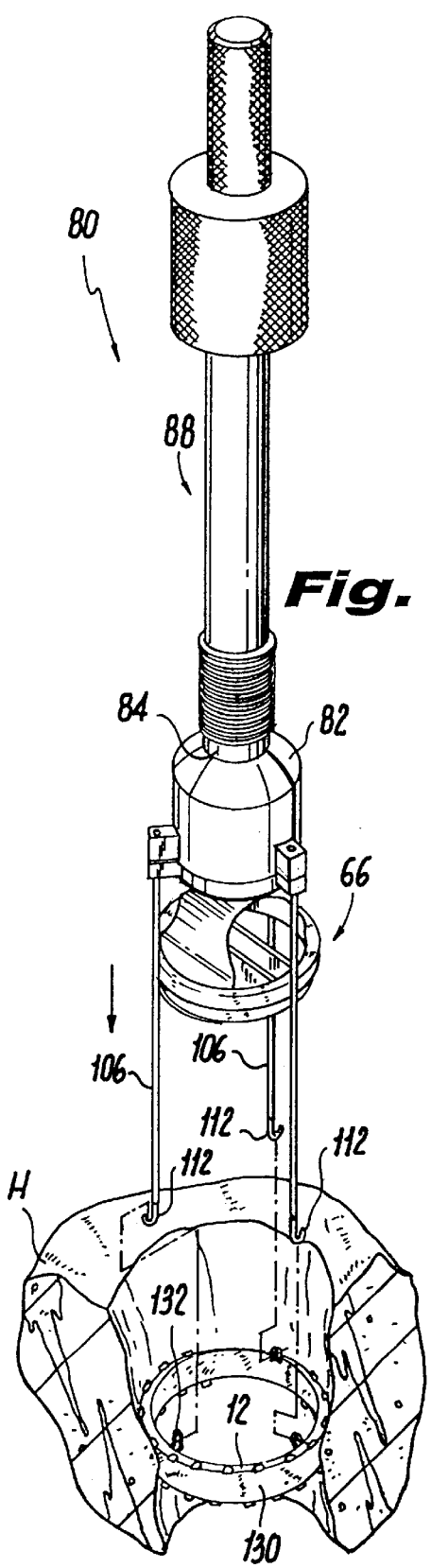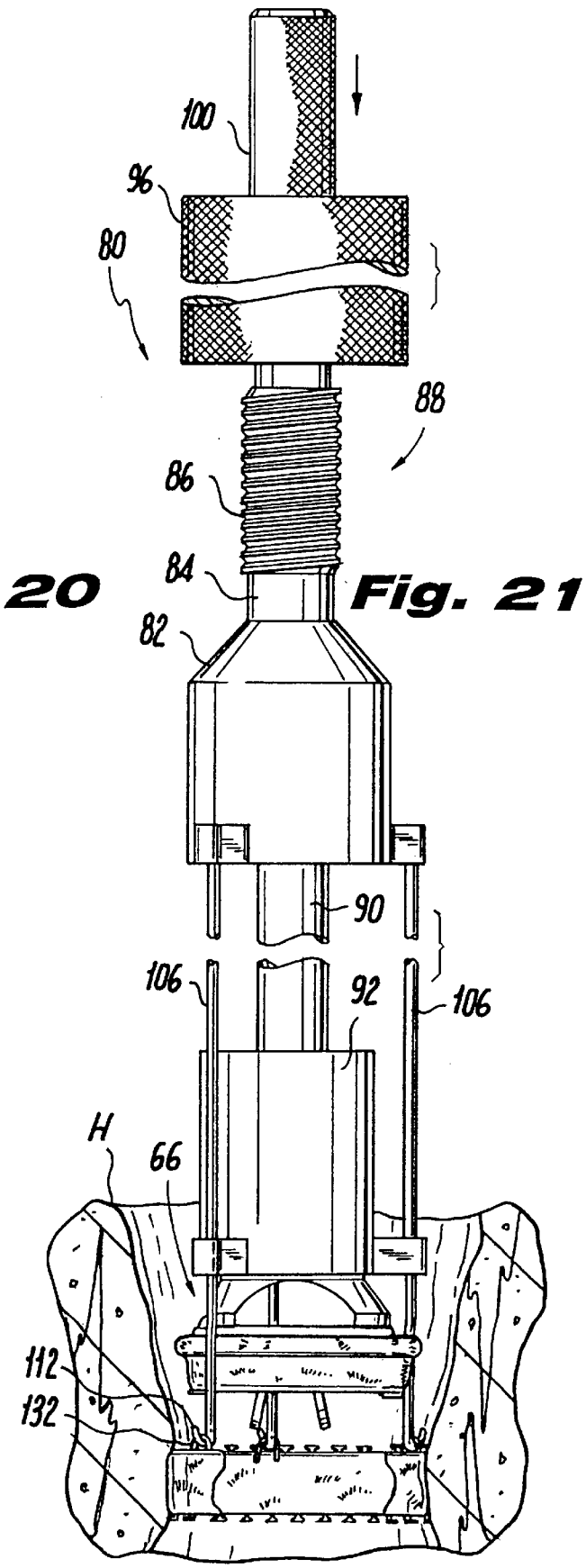

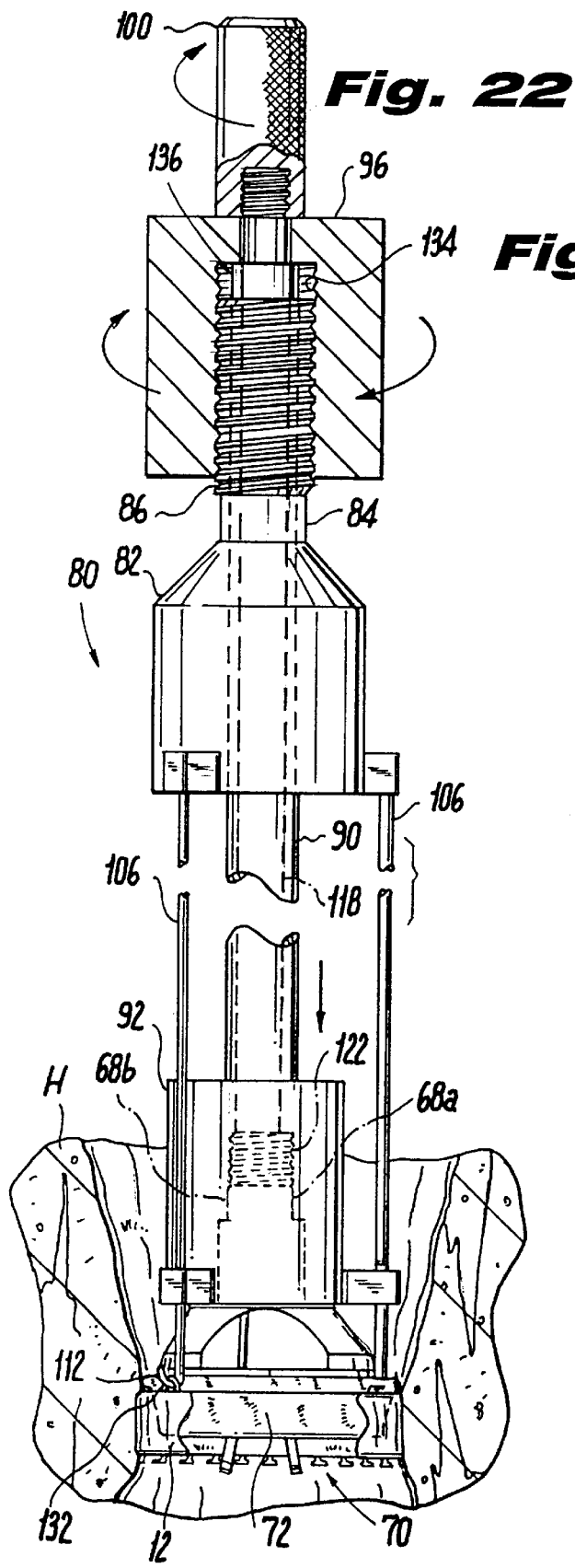
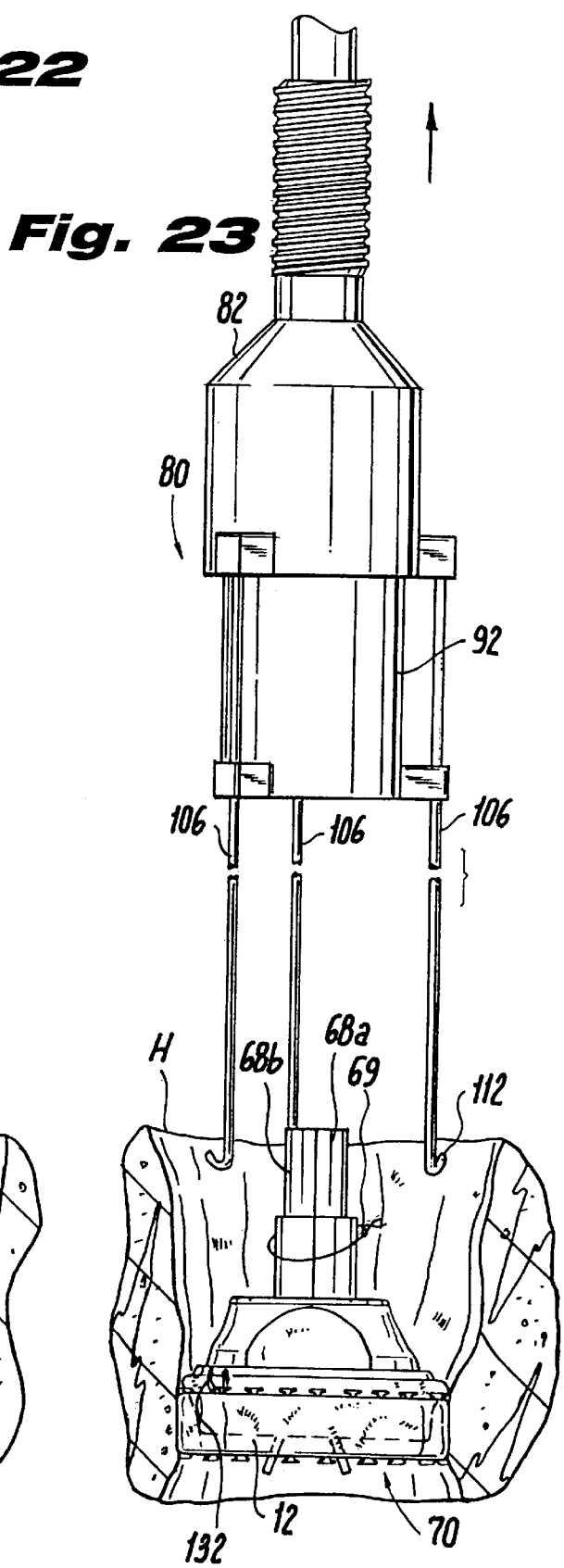

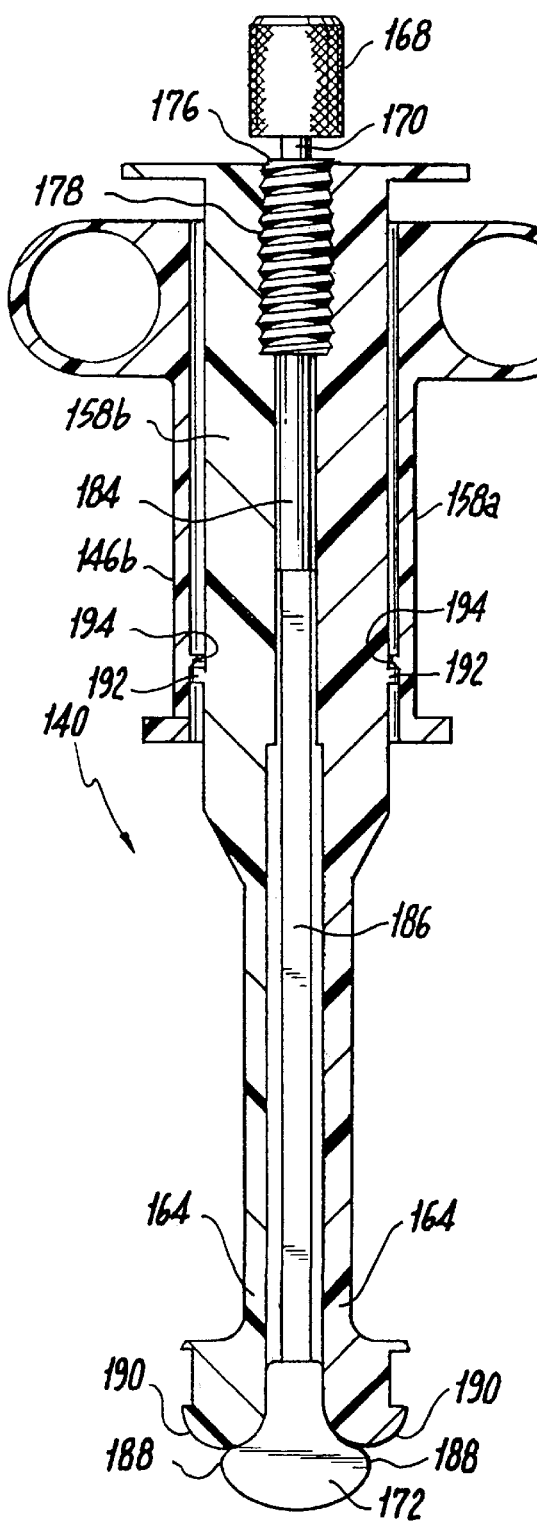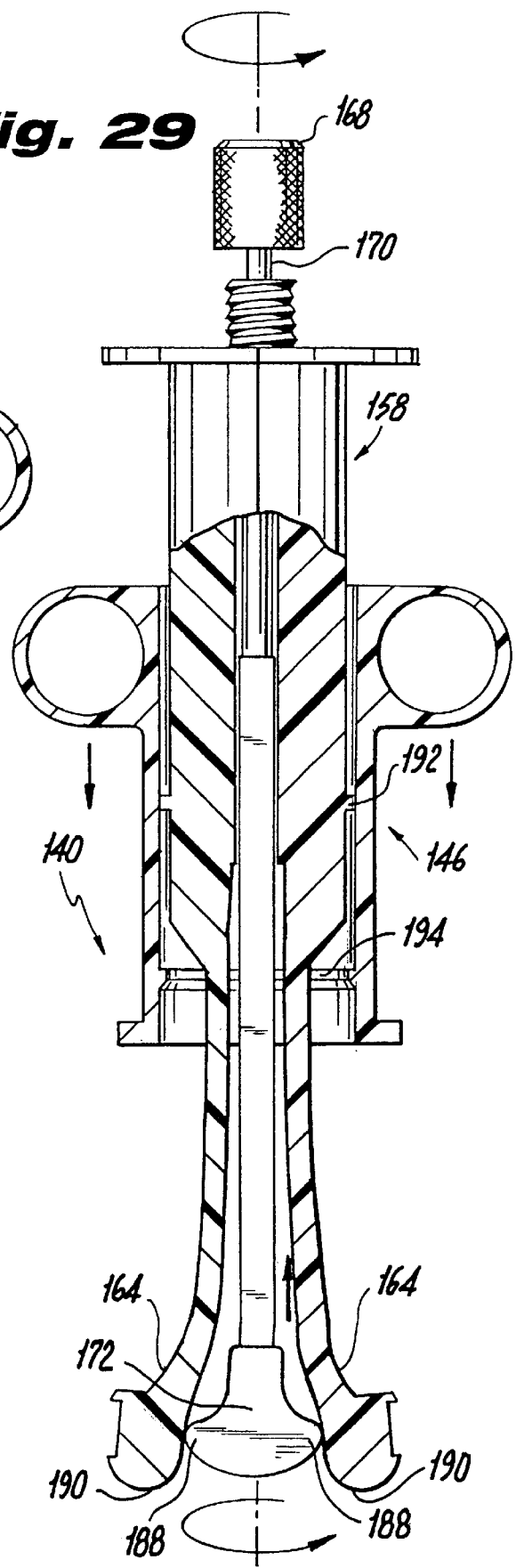

HEART VALVE REPLACEMENT TOOLS AND PROCEDURES

BACKGROUND

1. Technical Filed

The subject disclosure relates to minimally invasive surgical procedures and apparatus and, more particularly, to instruments and methods for performing heart valve replacement surgery.

2. Background of Related Art

The diagnosis and treatment of coronary disease and related conditions often requires repair or replacement of the valves located within the heart. Various factors, such as, for example, calcification, may result in the mitral or aortic valves becoming impaired or functionally inoperative requing replacement. Where replacement of a heart valve is indicated, in general, the dysfunctional valve is cut out and replaced with either an artificial, synthetic heart valve or a harvested porcine heart valve. The replacement valve is typically sutured in place of the original valve.

It is common to access the heart in a patient's thoracic cavity by making a longitudinal incision in the chest. This procedure, referred to as a median sternotomy, includes cutting through the sternum and forcing the two opposing halves of the rib cage to be spread apart allowing access to the thoracic cavity and thus the heart.

Instruments particularly suitable for spreading and holding apart the halves of the rib cage are marketed by States Surgical Corporation, Norwalk, Connecticut. The MINI-CABG* UNIVERSAL BASE RETRACTOR includes a substantially planar base having an opening which can be positioned on the patient such that the opening overlies the incision at the operative site. Retractor blades, such as the MINI-CABG* retractors, are slidably mounted on the base and are provided to spread apart the rib cage halves and engage and retract obstructing tissue. The base may also be provided with surgical instruments which can be used to stabilize or manipulate die heart during surgery such as the MIN-CABG* HEART STABILIZER AND SITE MANIPULATOR.

Once access to the thoracic cavity has been achieved, surgery on the heart to effect valve replacement may be performed. During some procedures, the heart beat is arrested by infusion of a cardioplegic fluid, such as potassium chloride kcl), to paralyze the myocardium while blood flow circulation is maintained through known heart bypass techniques. Alternatively, the heart is allowed to-beat to maintain circulation, while a localized area of the heart, on which surgery is to be performed, is locally immobilized.

The heart is incised and the defective valve is cut away leaving a surrounding area of locally tougher tissue. Known heart valve replacement techniques typically include individually passing sutures through the tough tissue to form an array of sutures. Free ends of the sutures are extended out of the thoracic cavity and laid, spaced apart, on the patient's body. The free ends of the sutures are then individually threaded through an edge around the circumference of the replacement valve or a supporting cuff. Once all sutures have been run through the valve, all the sutures are pulled up taught and the valve is slid or "parachuted" down into place adjacent the tough tissue. Thereafter, the replacement valve is secured in place using the sutures.

Where replacement is performed utilizing an artificial valve, hand held instruments in the form of a stick may be affixed to the valve and used to manipulate the replacement valve into place. The commercially available replacement valves are typically provided with a detachable holder structure which can be engaged by the hand tools.

While the above described procedures are sufficient to successfully position a heart valve within the heart, they are particularly time consuming. Therefore, a need exists for apparatus and procedures of quickly and efficiently positioning and affixing artificial heart valves within the heart.

SUMMARY

There are provided various embodiments of systems and methods for installing a synthetic, artificial heart valve within a patient. The first system generally includes two assemblies such as an expandable ring installation assembly and a heart valve installation assembly. A separate tool is associated with each assembly. The ring installation assembly includes a ring installation tool which is provided to releasably engage an expandable heart valve ring. The ring, when positioned at the site of the removed natural heart valve, can be expanded into place so as to engage tissue and form an anchor for later insertion of the heart valve. The ring installation tool includes structure for releasably holding the expandable heart valve ring and camming structure for expanding the expandable heart valve ring from a first diameter to an increased second diameter and into engagement with tissue.

The novel heart valve ring utilized with the first assembly generally includes an elongated strip of metallic or biocompatible material having a plurality of latches which are configured to engage corresponding openings in the material when-manipulated to form a ring. The latches and openings operate in ratchet form to maintain heart valve ring in an expanded condition. Additionally, the heart valve ring may preferably be provided with tabs extending generally perpendicularly to the surface of the ring. The tabs are provided to engage tissue so as to assist in anchoring the heart valve ring to tissue and to secure the heart valve to the heart valve ring. Additionally, the heart valve ring may include inwardly projecting teeth which are configured to engage a heart valve or a cuff surrounding a heart valve to assist in holding the heart valve to the expandable ring.

The second assembly or heart valve installation assembly includes a second tool or valve installation tool which is configured to releasably hold a synthetic heart valve, which typically includes its own heart valve holder structure, and position the heart valve within the expanded heart valve ring. The valve installation tool includes a valve positioner which is movable relative to a housing of the tool so as to drive the heart valve into engagement with the expandable ring. Preferably, the heart valve installation tool includes a release mechanism for releasing the heart valve once it has been positioned within the heart valve ring and grasping structure so as to engage the housing of the heart valve installation tool in stationary relationship relative to the heart valve ring.

A method of installing a heart valve within a patient utilizing the first system is provided and generally includes positioning an expandable heart valve ring on a ring installation tool and positioning the heart valve ring at the operative site within the patient's heart. Preferably, the expandable heart valve ring is provided with a synthetic graft material surrounding it so as to facilitate continuing growth and securement to the heart valve tissue. The heart valve ring is subsequently expanded into engagement with the heart tissue and is released from the heart valve installation tool. The heart valve ring installation tool is preferably removed from the operative site. A valve installation tool containing an artificial heart valve, preferably having valve holder structure such as two members (halves) for engaging the valve, is positioned adjacent the expanded heart valve ring. Preferably, grasping structure on the valve installation tool is engaged with the expanded heart valve ring and the valve positioner is actuated so as to drive the heart valve into engagement with the heart valve ring. Once the heart valve has been affixed within the heart valve ring a release mechanism may be actuated to release the heart valve from the valve installation tool and the valve installation tool removed from the operative site. Subsequently, a suture holding the valve holder halves may be cut to release the valve holder halves supplied with the artificial heart valve and removed from the operative site.

In a second system, the expandable ring installation assembly and the heart valve installation assembly are provided together in a single or "one shot" tool. The valve installation assembly generally includes a housing having structure for frictionally retaining a synthetic heart valve thereon. Notably, the heart valve holder generally supplied with the heart valve is not utilized in the second system. A ring installation assembly is movable relative to, and extends generally through, the valve installation assembly. The ring installation assembly includes structure at a distal-most end for releasably retaining the expandable heart valve ring. Camming structure is provided on the ring installation assembly for expanding the expandable heart valve ring into engagement with the heart tissue.

A method of utilizing a second system generally includes accessing the heart and positioning the system such that the expandable heart valve ring is adjacent the operative site. The tool may then be actuated to expand the expandable heart valve ring into engagement with the tissue. This occurs by moving camming structure associated with the ring installation assembly relative to the expandable heart valve ring. Once the heart valve ring has been expanded, the tool may be actuated to reverse the camming structure such that the holding structure may be passed downwardly through the heart valve ring. Thereafter, the valve installation assembly is actuated to drive the artificial heart valve down into engagement with the expandable heart valve ring. As noted above, preferably the expandable heart valve ring includes teeth to engage a cuff provided with the expandable heart valve. Once the heart valve has been installed within the heart valve ring, the second system may be removed by drawing the expanding and camming structure through the heart valve and out of the operative site.

BRIEF DESCRIPTION OF THE DRAWINGS

Various embodiments are described herein with reference to the drawings, wherein:

FIG. 18 is a view similar to FIG. 17 and illustrating release of the ring expander tool from the expanded heart valve ring;

FIG. 19 is a view illustrating removal of the ring expander tool from the operative site with the expanded heart valve ring fixed in place within the heart tissue;

FIG. 20 is a perspective view of the heart valve installation assembly being moved into the operative site;

FIG. 21 is a view illustrating the engagement of the heart valve installation tool with the implanted and expanded heart valve ring and advancement of a heart valve assembly toward the expanded heart valve ring;

FIG. 22 is a view similar to FIG. 21 illustrating actuation of the heart valve installation tool to position the heart valve assembly within the expanded heart valve ring;

FIG. 23 is a view of the heart valve installation tool detached from the heart valve assembly and expanded heart valve ring;

FIG. 28 is a sectional view of the single shot instrument;

FIG. 29 is a view, partially shown in section of the single shot instrument during actuation;

DETAILED DESCRIPTION OF THE PREFERRED EMBODIMENTS

Various embodiments are disclosed herein which relate to installation systems including tools and methods for positioning and securing a synthetic replacement heart valve within the heart without the necessity of manually suturing the valve in place. The disclosed systems accomplish this by implanting a base or anchor in the form of an expandable ring into the heart tissue and to which the synthetic heart valve may be affixed. In a first embodiment, a two tool installation system is provided which generally includes a ring installation assembly and a separate heart valve installation assembly.

Figure 1:
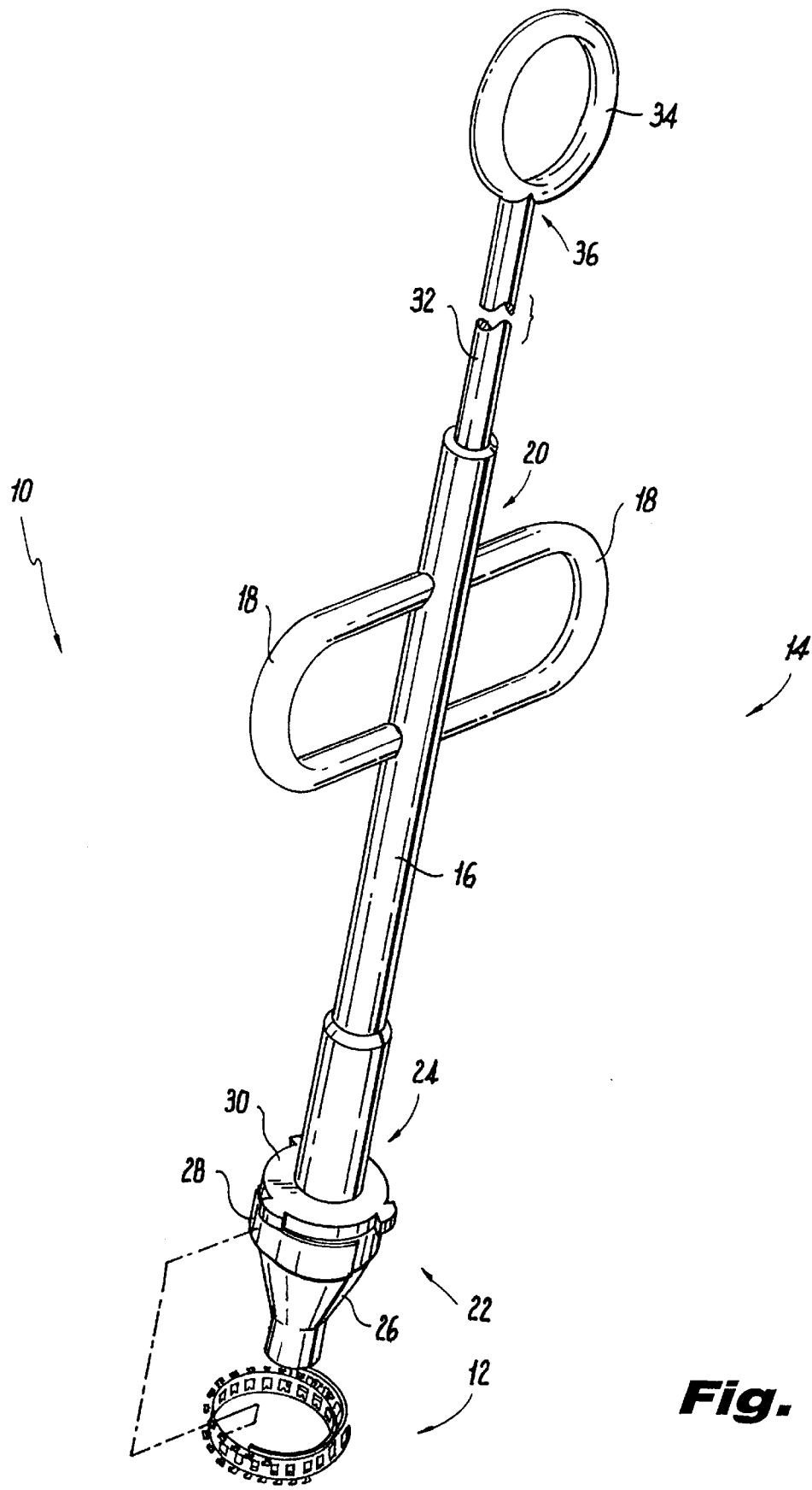
FIG. 1 is a perspective view of an expandable heart valve ring installation assembly which forms part of a two-part heart valve installation system.

Referring now to FIG. 1, there is disclosed a ring installation assembly 10 which includes a novel heart valve ring 12 and a ring expander tool 14 which is provided to implant heart valve ring 12 within the heart tissue. Ring expander tool 14 includes a housing 16 having a pair of handles 18 at a proximal end 20 thereof. An expander assembly 22 is provided on distal end 24 of housing 16. Expander assembly 22 is provided to releasably engage heart valve ring 12 and expand heart valve ring 12 in a manner described hereinbelow. As used herein, the term "distal" refers to that portion of the assembly, or component thereof, further from the user while the term "proximal" refers to that part of the assembly, or component thereof, closer to the user.

Expander assembly 22 generally includes a nose cone 26 and an expansion sleeve 28 surrounding nose cone 26. Expansion sleeve 28 is preferably formed of a shape memory or spring steel material and is configured to assume a reduced diameter at rest. A back plate 30 is provided adjacent distal end 24 of housing 16 to maintain heart valve ring 12 in position about expansion sleeve 28. Ring expander tool 14 additionally includes a plunger 32 which is slidably mounted within housing 16 and is provided to actuate expander assembly 22. Plunger 32 has a handle 34 at a proximal end 36 thereof. Movement of plunger 32, distally and proximally, relative to housing 16 causes expansion sleeve 28 to be expanded and reduced, respectively, in diameter in a manner described hereinbelow so as to expand and release heart valve ring 12.

Figure 2:
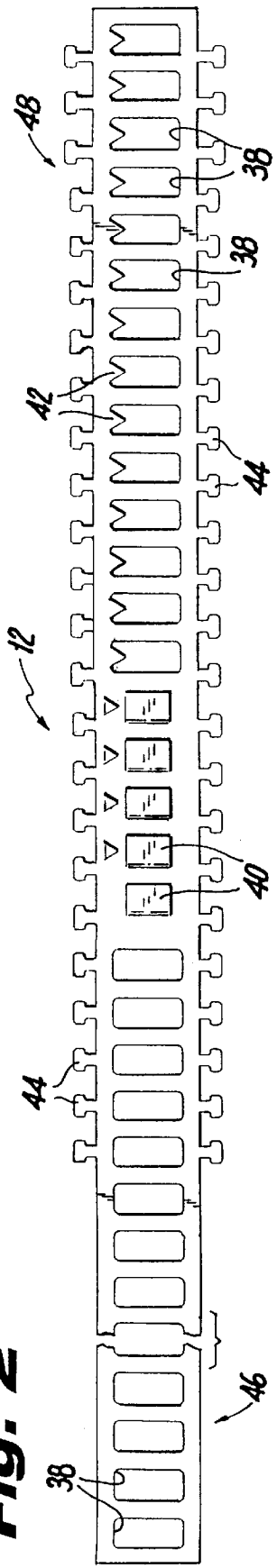
FIG. 2 is a plan view of a first side of an expandable heart valve ring in a flat configuration prior to being manipulated to form a ring.

As noted hereinabove, ring installation assembly 10 includes a novel heart valve ring 12 which is radially expandable to engage heart tissue and thereby provide a base or anchor for securing a synthetic heart valve thereto. Expandable heart valve ring 12 is generally formed as a strip of suitable biocompatible material such as, for example, stainless steel. Heart valve ring 12 is manipulatable from a strip to a ring. Referring now to FIG. 2, a plurality of openings 38 are provided along the length of heart valve ring 12. Latches 40, located generally centrally within heart valve ring 12, are provided to engage openings 38 in ratchet fashion so as to secure heart valve ring 12 in an expanded position. In order to facilitate securing heart valve ring 12 to the walls of heart tissue, opposed tabs 44 are provided along the edges of heart valve ring 12 and are configured to penetrate and engage heart tissue. There are also provided a plurality of teeth 42 which engage a heart valve or cuff thereon once the heart valve has been positioned within heart valve ring 12. Openings 38 and latches 40 as well as teeth 42 and tabs 44 may be formed in a strip of suitable heart valve ring material by die punching. Other methods of forming the heart valve ring, such as, molding, machining, etc. are also contemplated.

Figure 4:
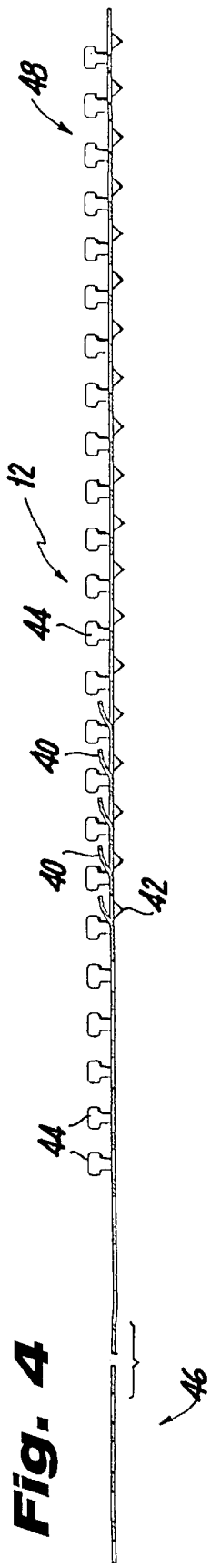
FIG. 4 is a sectional view of the expandable heart valve ring taken along line 4—4 of FIG. 3.
Figure 5:
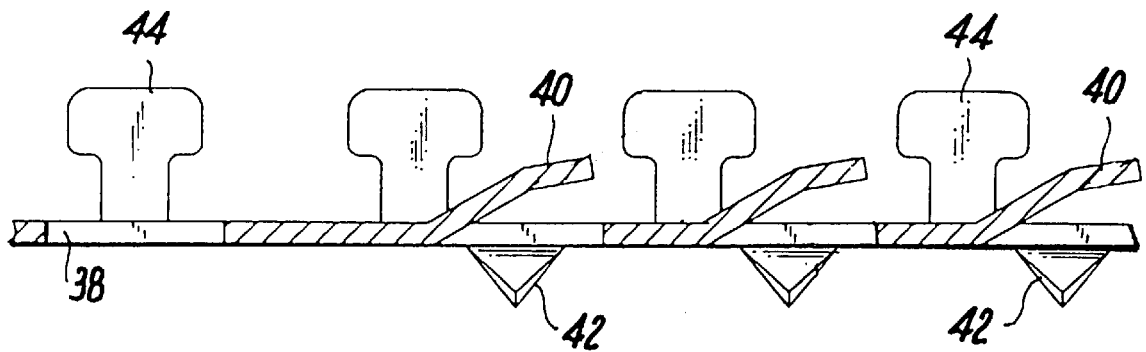
FIG. 5 is a partial sectional view of the expandable heart valve ring taken along line 5—5 of FIG. 3.
Figure 24:
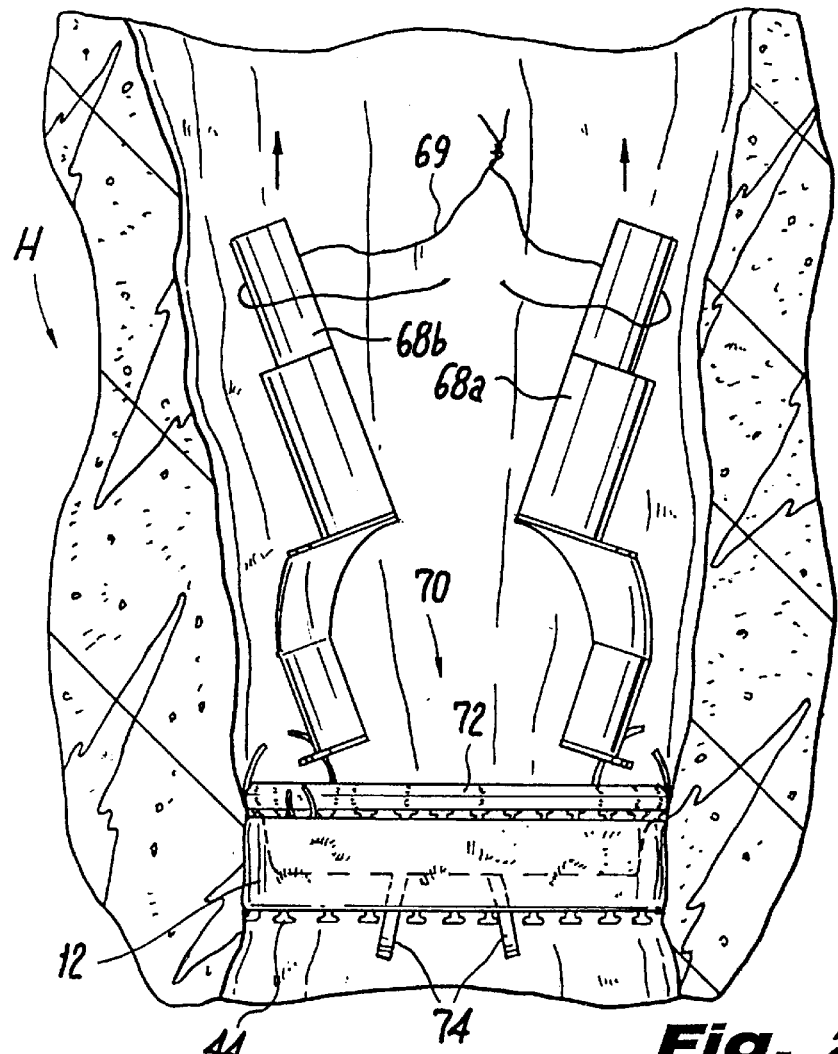
FIG. 24 is a view of a heart valve holder being removed from a heart valve.

As shown in FIGS. 24, a first end 46 of heart valve ring 12 is generally devoid of tabs 44 while a second end 48 of heart valve ring 12 includes tabs 44. This is to provide a degree of overlap as first end 46 is positioned within second end 48 when manipulated to form a ring so as to avoid duplicate tabs 44 projecting and overlapping each other. As shown in FIGS. 4 and 5, when folded over, tabs 44 project from heart valve ring 12 in a first direction to engage tissue while teeth 42 project from heart valve ring 12 in an opposite direction to engage a heart valve. Latches 40 generally project from heart valve ring 12 in the same direction as tabs 44.

Figure 6:
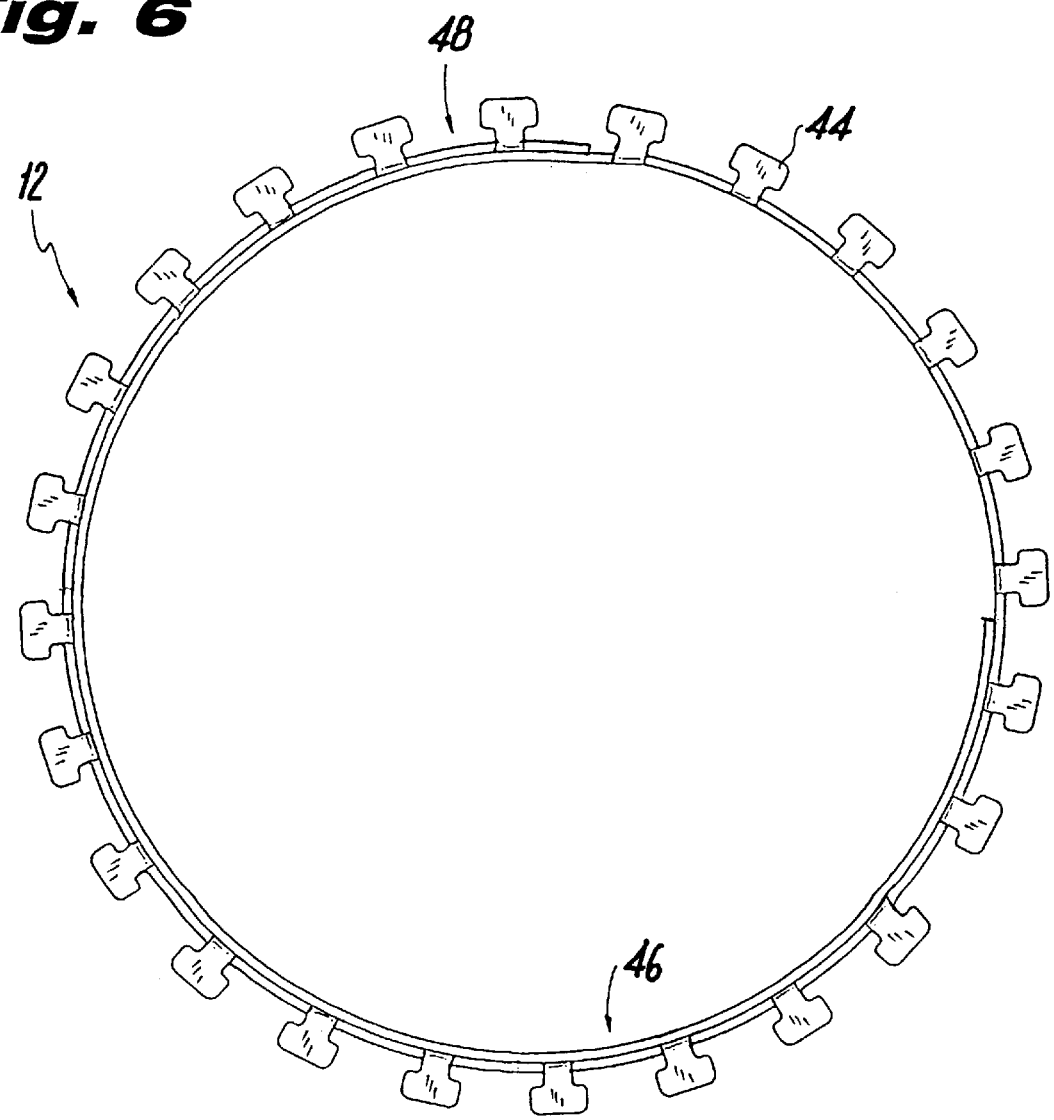
FIG. 6 is an end view of the expandable heart valve ring manipulated to form a ring.

Referring now to FIG. 6, there is illustrated heart valve ring 12 manipulated to form a generally circular ring with first end 46 generally on the interior of the ring and second end 48 generally facing exteriorly of the ring.

Figure 7:
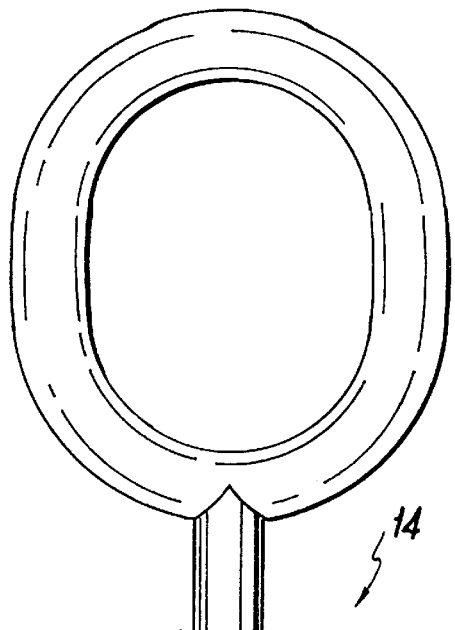
FIG. 7 is a perspective view of a ring expander tool of the assembly of FIG. 1.
Figure 8:
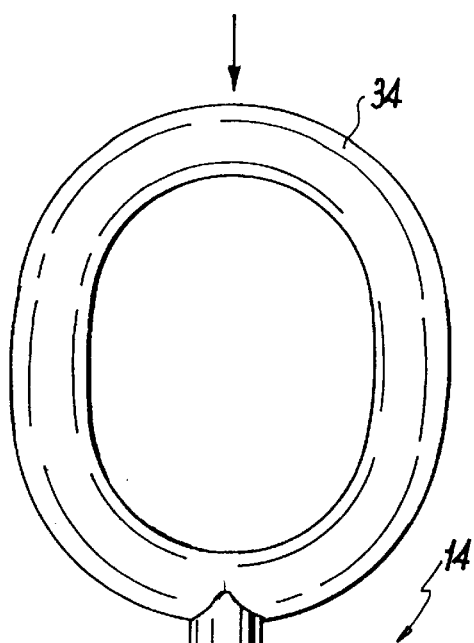
FIG. 8 is a partial sectional view of the ring expander tool of FIG. 7 in an actuated condition.

Referring now to FIGS. 7 and 8, in order to actuate ring expander tool 14 and expand heart valve ring 12 from a generally reduced state to an expanded state, expander assembly 22 generally includes a tapered wedge 50 which is provided at a distal end 52 of plunger 32. A stop 54 extends distally from tapered wedge 50. Tapered wedge 50 is movable within a tapered bore 56 formed in nose cone 26 in response to movement of plunger 32. An abutment surface 58 is provided at a distal end of nose cone 24 to engage stop 54 on plunger 32 (FIG. 8).

Figure 9:
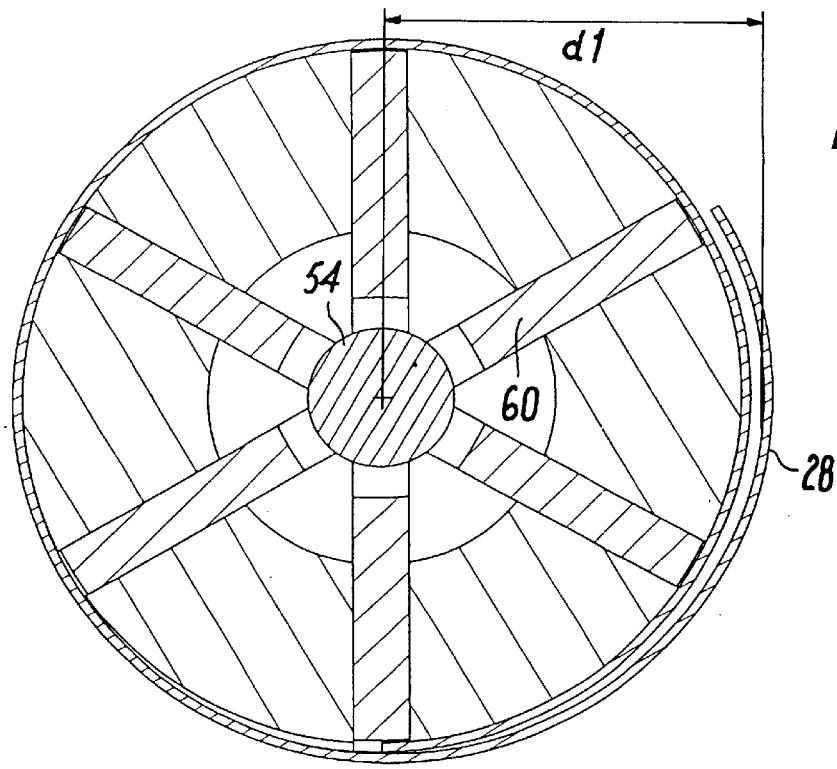
FIG. 9 is a sectional view taken along line 9—9 of FIG. 7.
Figure 10:
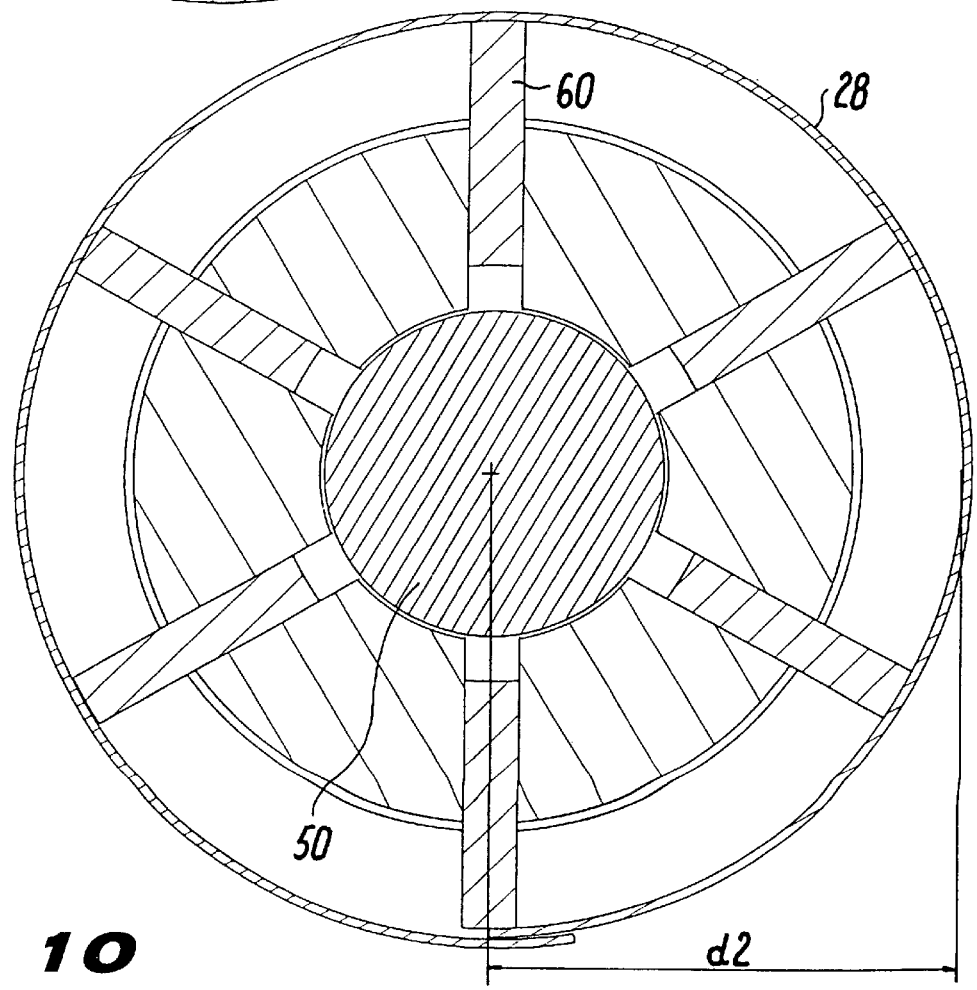
FIG. 10 is a sectional view taken along line 10—10 of FIG. 8.

Referring now to FIGS. 7–10, a plurality of radially projecting walls 60 are provided within slots 62 formed in nose cone 26. Walls 60 are configured to engage tapered wedge 50 as tapered wedge 50 is moved distally. Thus, as shown in FIGS. 7 and 9, when plunger 32 is in a proximal position, tapered wedge 50 does not engage walls 60 and expansion sleeve 28 remains in a reduced first diameter "d1". However, as shown in FIGS. 8 and 10, as plunger 32 is driven distally with respect to housing 16, tapered wedge 50 drives walls 60 outwardly to thereby force expansion sleeve 28 radially outwardly to an expanded second diameter "d2" greater than that of the first diameter.

Figure 11:
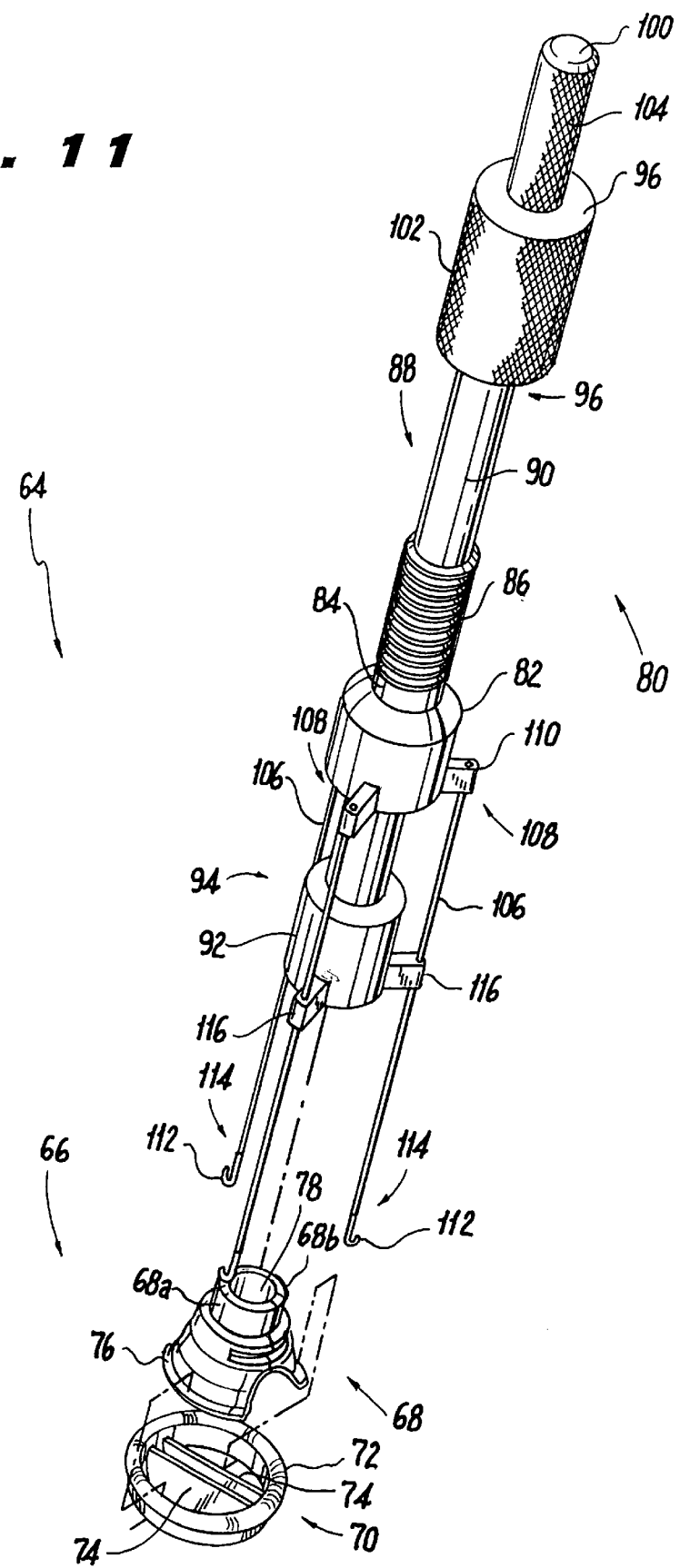
FIG. 11 is a perspective view of a heart valve installation assembly which forms a second part of the two-part heart valve installation system.

Referring now to FIG. 11, there is disclosed a heart valve installation assembly 64 associated with the two-part heart valve installation system. Heart valve installation assembly 64 generally includes a heart valve assembly 66. Heart valve installation assembly 66, generally includes a holder 68 which is preferably formed in holder halves 68a and 68b and a heart valve 70. Heart valve 70 generally includes an outer ring or cuff 72 having a plurality of leaflets 74 pivotally mounted therein. Flanges 76 on holder halves 68a and 68b are configured to engage interior edges of ring 72 to hold heart valve 70 in position for surgery. Holder halves 68a and 68b define a bore 78 therebetween which is configured to engage structure on a valve installation tool.

Heart valve installation assembly 64 additionally includes a valve installation tool 80. Valve installation tool 80 is provided to position heart valve 70 within expandable ring 12. Installation tool 80 includes a housing 82 having a shaft 84 extending proximally therefrom. Shaft 84 is formed with a threaded surface 86. Valve installation tool 80 additionally includes a valve positioner 88 slidably mounted relative to housing 82. Specifically, a drive shaft 90 of valve position 88 is slidably mounted within housing 82 and includes a valve driver 92 positioned at a distal end 94 of drive shaft 90. A drive knob 96 is positioned at a proximal end 98 of drive shaft 90. Drive knob 96 is affixed to drive shaft 90 such that drive knob 96 is free to rotate relative to drive shaft 90. Valve positioner 88 is also provided with a release mechanism including a release knob 100. Drive knob 96 and release knob 100 are provided with knurled surfaces 102, 104, respectively, to facilitate operation by the user.

At least one, and preferably three, guide bars 106 are affixed at their proximal ends 108 to wings 110 formed on housing 82. Guide bars 106 extend distally from wings 110 and terminate in hooks 112 formed at distal ends 114 of guide bars 106. Hooks 112 are provided to engage heart valve ring 12 once heart valve ring 12 has been imbedded into tissue. By engaging heart valve ring 12 with hooks 112, housing 82 is positioned stationary relative to heart valve ring 12 and permits movement of valve positioner 88 and heart valve assembly 66 without displacing heart valve ring 12. Wings 116 are provided on valve driver 92 and are slidably mounted over guide bars 106 to facilitate alignment and positioning of valve assembly 66, carried by valve driver 92, relative to heart ring 12.

Figure 12:
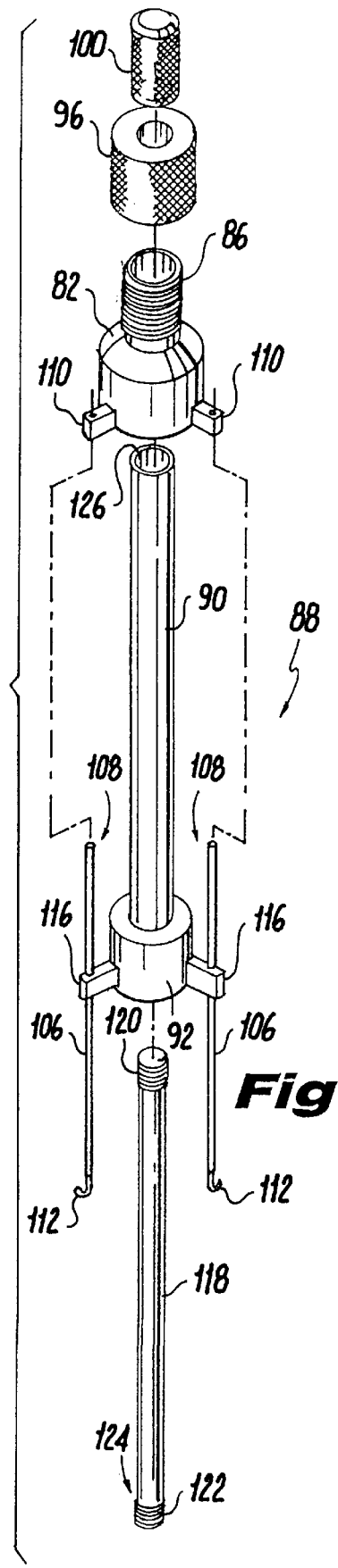
FIG. 12 is a view, with parts separated, of a heart valve installation tool of the assembly of FIG. 11.

As shown in FIG. 12, valve positioner 88 additionally includes a release shaft 118 which is slidably mounted within drive shaft 90. A threaded proximal end 120 of release shaft 118 engages release knob 100 to affix release shaft 118 to release knob 100. A threaded surface 122 is provided at a distal end 124 of release shaft 118 and is configured to engage a portion of valve holder 68. Release shaft 118 is slidably mounted within a bore 126 of drive shaft 90.

Figure 13:
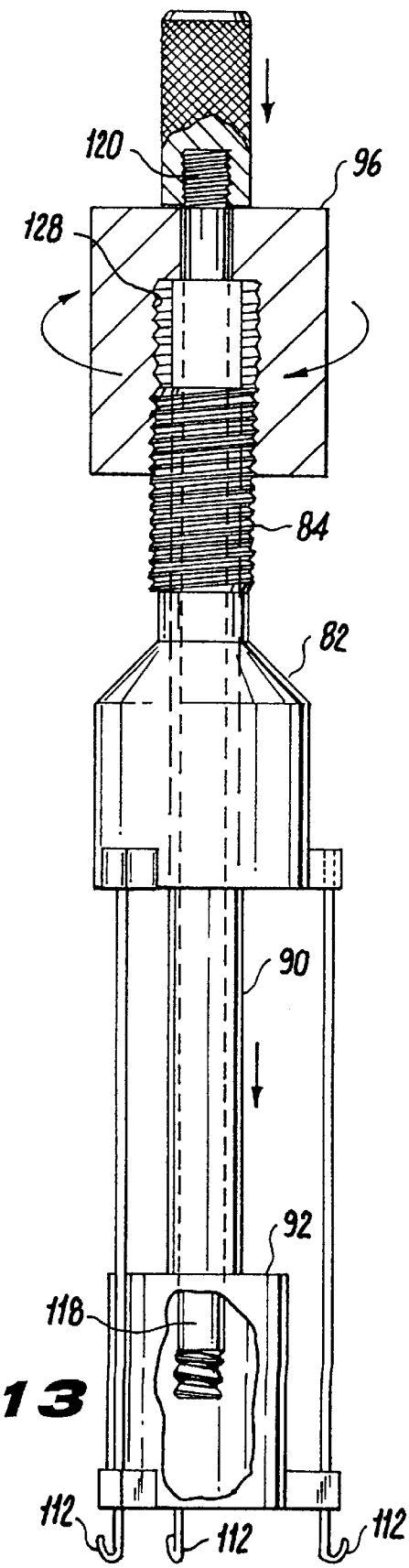
FIG. 13 is a partial sectional view of the heart valve installation tool in an actuated state.

Referring now to FIG. 13, drive knob 96 is provided with a threaded inner surface 128 which, when positioned adjacent shaft 84 of housing 82, engages threaded surface 86. Thus, by rotating drive knob 96 relative to housing 82, drive shaft 90 and thus valve driver 92 can be moved in precise and definite amounts relative to hooks 112 and thus expand heart valve ring 12.

Figure 14:
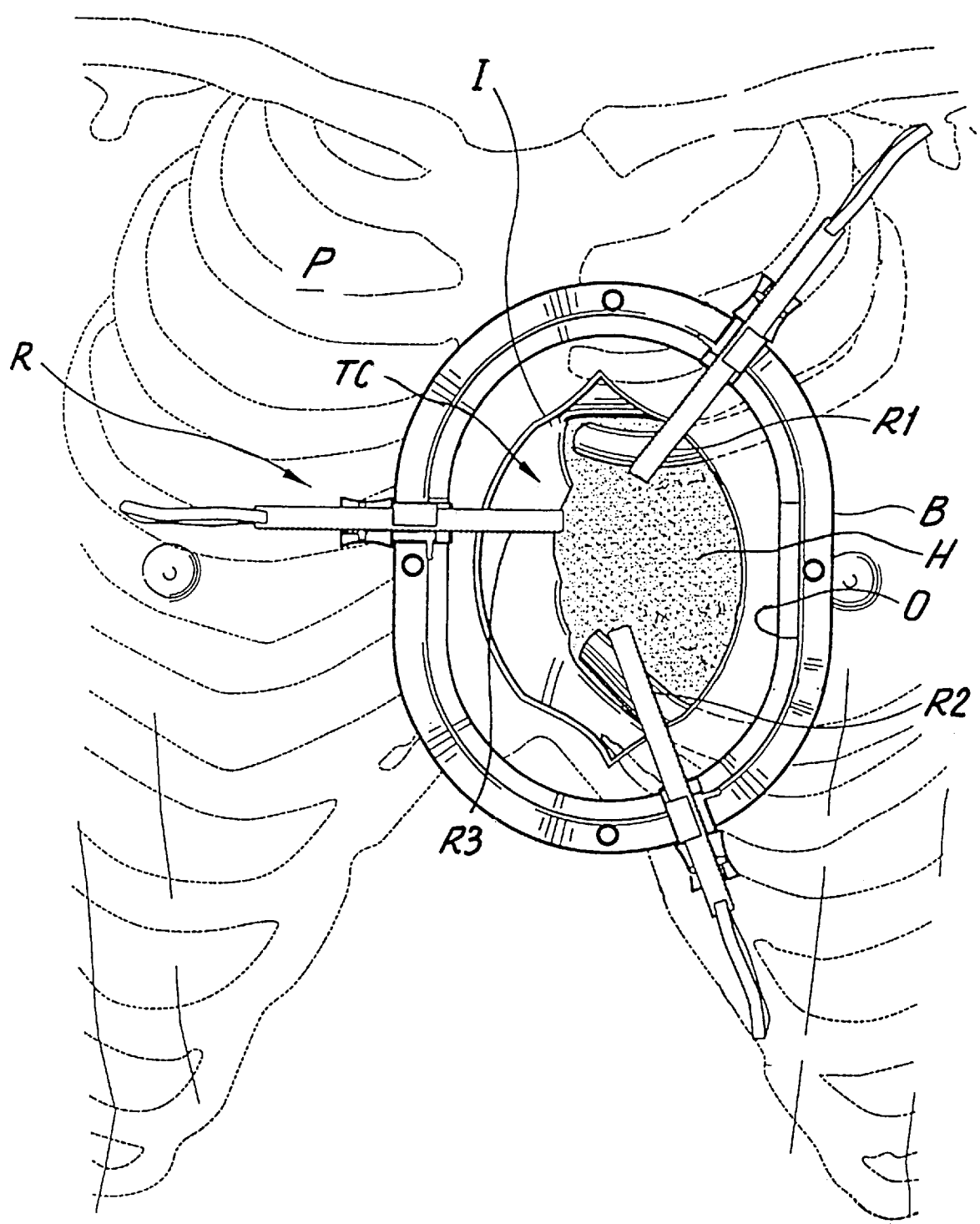
FIG. 14 is a perspective view of a patient with access to the thoracic cavity held open by a retractor.

With reference to FIGS. 14–25, the method of using the two tool installation system to install an artificial heart valve within a patient will now be described. Referring initially to FIG. 14, access to the heart through the thoracic cavity is accomplished using well known surgical procedures. Generally, an incision I is made through the sternum of a patient P to access the thoracic cavity TC and expose the heart H.

Preferably, access to the cavity is maintained with the assistance of a retractor R. Retractor R generally includes an oval planar base B. Retractor R is positioned on patient P such that an opening O defined by base B overlies incision I. A plurality of retractor blades R1, R2, R3 . . . are slidably mounted on base B and engage and retract the tissue edges of incision I. Optionally, additional instruments may be affixed to base B to manipulate and/or stabilize the heart H to facilitate surgery thereon. Blood flow circulation is maintained using known techniques. Thus, access to heart H is achieved and maintained. Other known open surgical procedures to access the heart are also contemplated and may be substituted for the procedure described herein.

Figure 15:
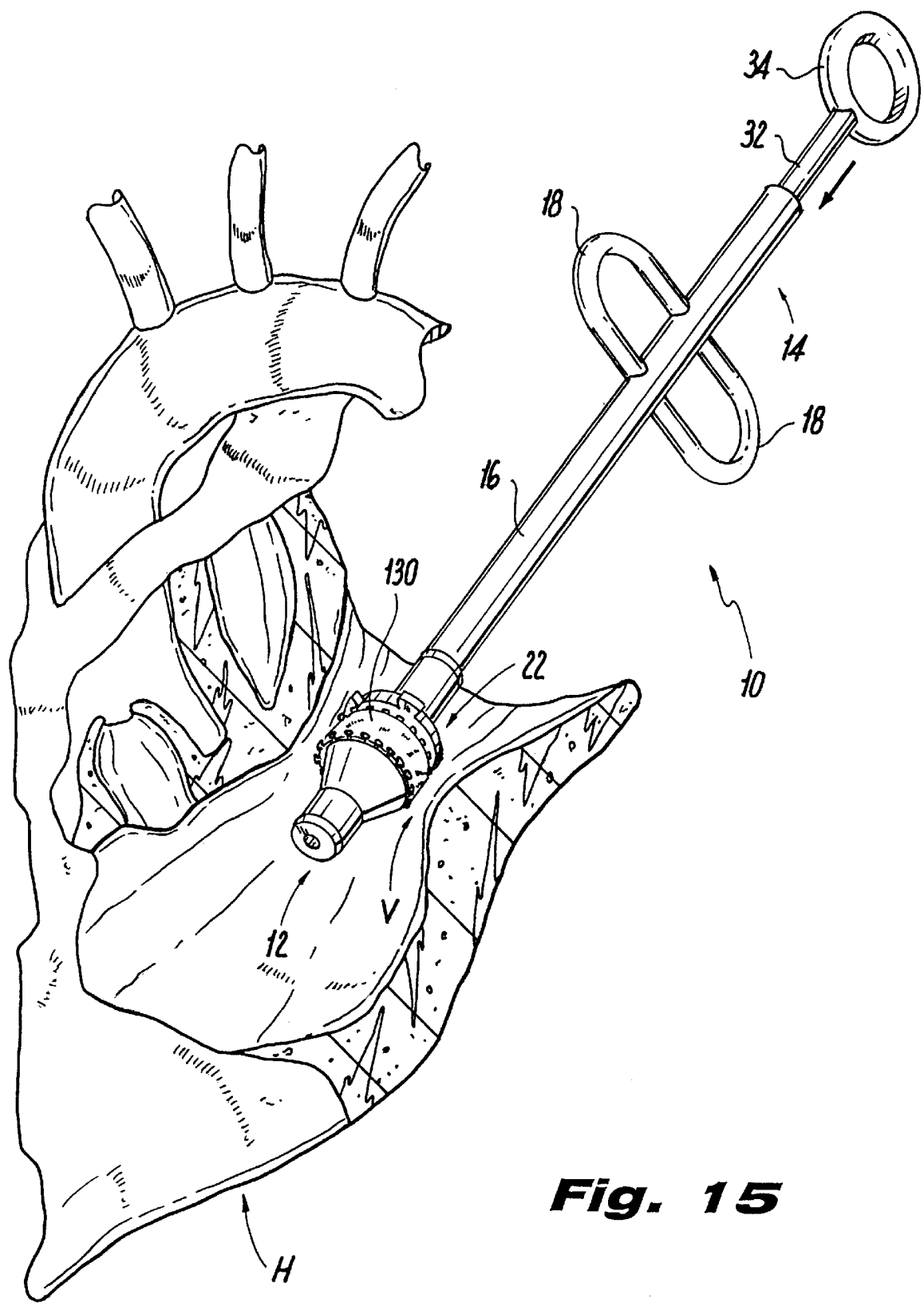
FIG. 15 is a perspective view of a heart with natural valve removed and the assembled ring expander tool and expandable heart valve ring in position to be actuated.

Once access to heart H has been obtained, heart H is opened and the dysfunctional valve is removed using known surgical procedures. Referring now to FIG. 15, ring installation assembly 10 is prepared by positioning heart valve ring 12 about expander assembly 22. Preferably, a natural or synthetic graft material 130 is placed around heart valve ring 12. Graft material 130 protects both heart H and heart valve ring 12 and facilitates tissue ingrowth to assist in holding heart valve ring 12 in place within the heart after expansion.

Ring installation assembly 10 is then manipulated to position expander assembly 22, and thus heart valve ring 12, within the space V between the chambers of heart H previously occupied by the dysfunctional valve. When heart valve ring 12 is in the appropriate position within space V, ring expander tool 14 is actuated by moving plunger 32 distally relative to housing 16 to expand heart valve ring 12.

Figure 3:
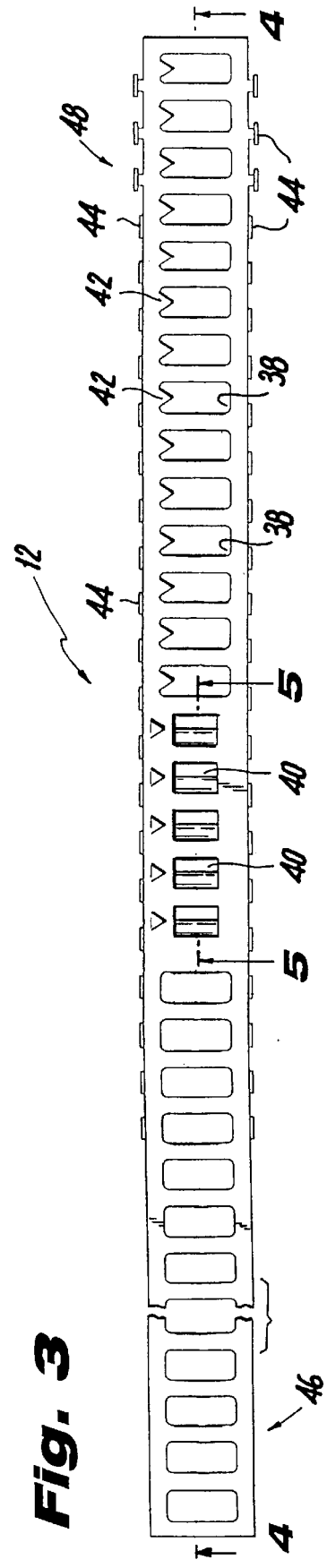
FIG. 3 is a plan view of a second side of the expandable heart valve ring of FIG. 2.
Figure 17:
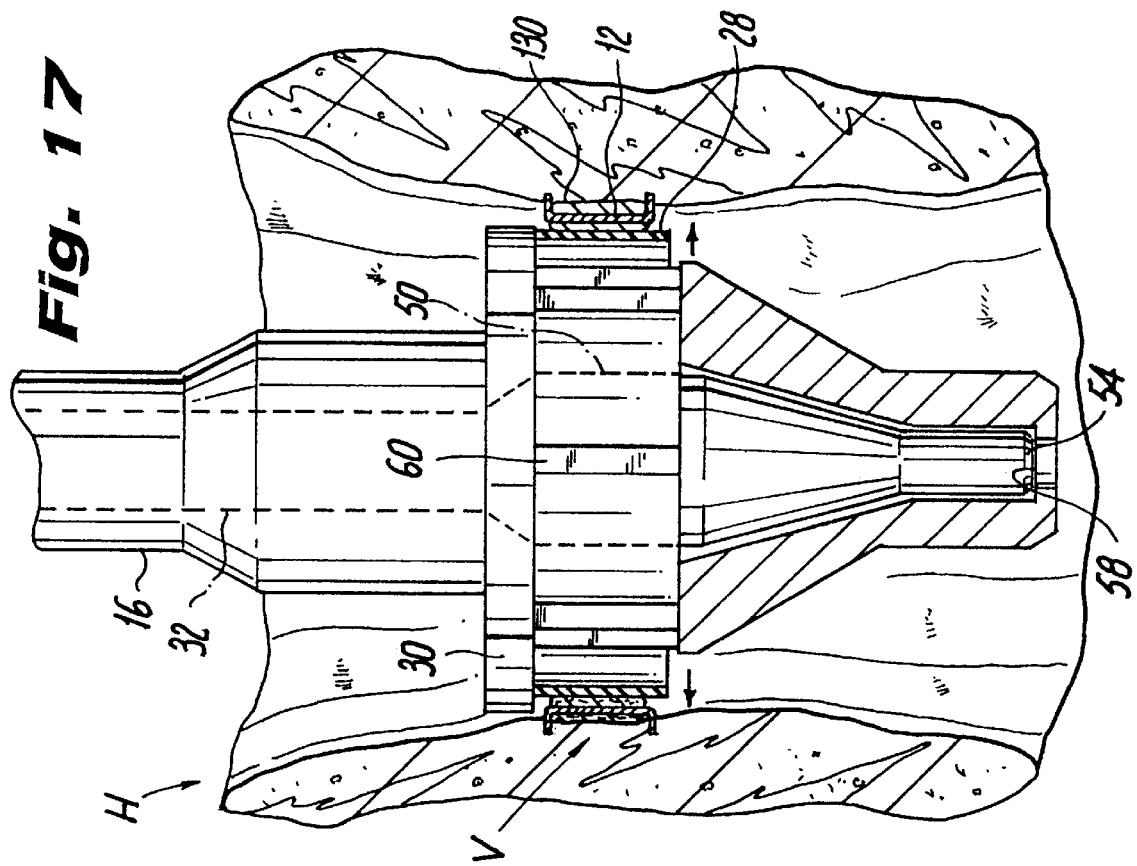
FIG. 17 is a view similar to FIG. 16 and illustrating expansion of the expandable ring into engagement with the surrounding tissue.
Figure 16:
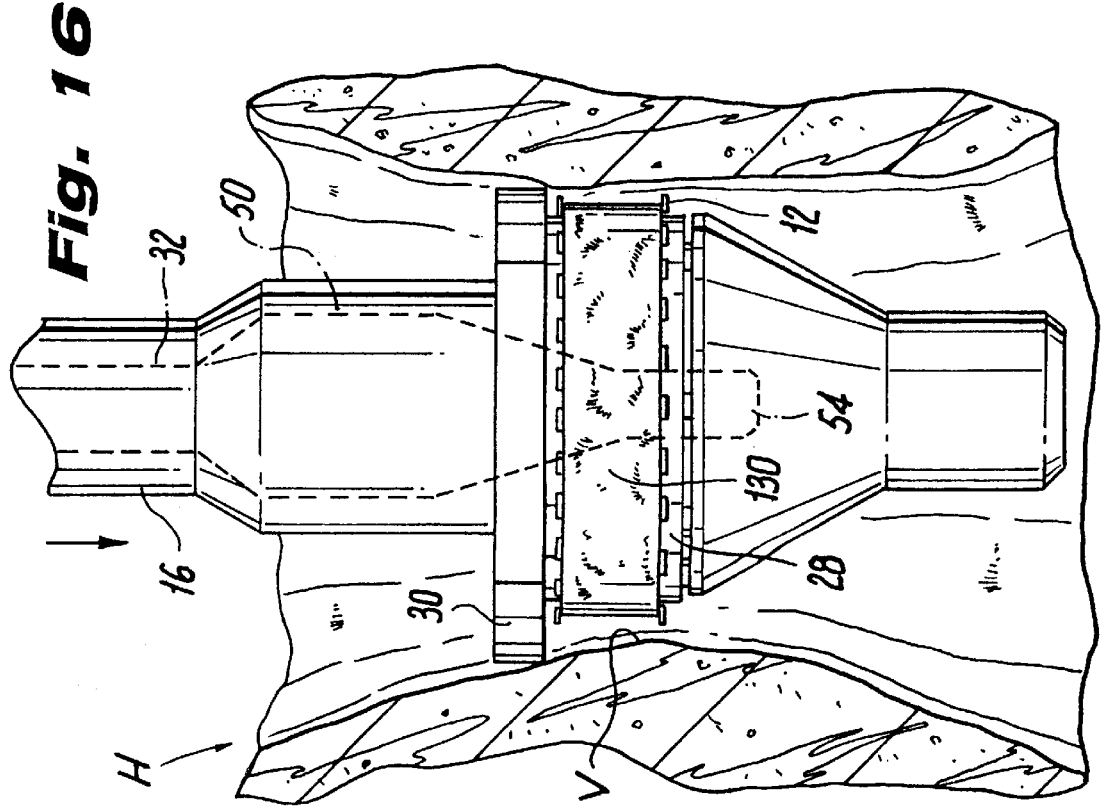
FIG. 16 is an enlarged view of the distal end of the ring expander tool positioned at the operative site.

Specifically, as shown in FIGS. 16 and 17, as plunger 32 is driven distally within housing 16, tapered wedge 50 engages and drives walls 60 radially outward forcing expansion sleeve 28 and thus heart valve ring 12 to move from an unexpanded state (FIG. 16) to an expanded state (FIG. 17). As heart valve ring 12 expands, it engages the heart tissue and wedges itself against the tissue. As noted hereinabove, latches 40 engage openings 38 (FIG. 3) to maintain heart valve ring 12 in the expanded state. Additionally, tabs 44 may become imbedded in the heart tissue to assist in securing heart valve ring 12 within space V in heart H. Distal advancement of tapered wedge 50 can be stopped when heart valve ring 12 is sufficiendy wedged against heart H. Maximum expansion is obtained when stop 54 engages abutment surface 58 (FIG. 17).

It should be noted that variously dimensioned ring expander tools 14 may be provided to attain differing maximum expanded diameters depending on the ring size and type of replacement valve. Further, the final expanded diameter of heart valve ring 12 should be substantially the same diameter as the natural valve replaced and space V as well as being approximately the same diameter as, or slightly larger than, the diameter of the replacement valve. Plunger 32 can then be withdrawn proximally relative to housing 16 withdrawing tapered wedge 50 within bore 56.

Referring now to FIGS. 18 and 19, as noted above, expansion sleeve 28 is formed of a spring or shape memory material such that when tapered wedge 50 is moved proximally within tapered bore 56, expansion sleeve 28 shrinks to a reduced diameter. As shown in FIG. 19, heart valve ring 12, with graft material 130 thereon, remains imbedded in heart H while ring expander tool 14 may be withdrawn from the heart H.

Referring now to FIG. 20, once heart valve ring 12 has been positioned within the heart, the second tool of the two-part installation system, specifically valve installation tool 80, may be used to position valve assembly 66 within expanded heart valve ring 12. Preferably, heart valve ring 12 is provided with one or more suture loops 132 which are affixed to either heart valve ring 12 or to graft material 130. Suture loops 132 are configured to receive hooks 112 of valve installation tool 80 so that valve installation tool 80 may be secured in a stationary position with respect to heart valve ring 12. Initially, valve installation tool 80 is advanced towards heart valve ring 12 until hooks 112 provided on guide bars 106 securely engage suture loops 132. As shown in FIG. 21, once hooks 112 have been secured to suture loops 132, valve positioner 88 may be moved distally relative to housing 82 to drive valve assembly 66 towards heart valve ring 12. To do so, drive knob 96 is advanced distally relative to housing 82 such that drive shaft 90 and thus valve driver 92 are advanced toward heart valve ring 12. As noted hereinabove, guide bars 106 guide valve driver 92 along the lengths thereof. Valve positioner 88 is advanced distally with respect to housing 82 until drive knob 96 comes into contact with threaded surface 86 on shaft 84 of housing 82.

Referring now to FIG. 22, once drive knob 96 has reached threaded surface 86, drive knob 96 may be rotated such that a threaded interior surface 134 of a bore 136 in drive knob 96 threadingly engages threaded surface 86 of shaft 84 and moves drive shaft 90 distally. As noted above, drive knob 96 is configured to rotate independently of drive shaft 90. By engaging threaded interior surface 134 of drive knob 96 with threaded surface 86 of shaft 84, valve driver 92 and thus valve assembly 66 may be advanced in discreet and precise amounts relative to heart valve ring 12. Additionally, the engagement of drive knob 96 with shaft 84 allows an increased amount of force to drive ring 72 of heart valve 70 into position within heart valve ring 12. By securing hooks 112 to suture loops 132 and heart valve ring 12, heart valve ring 12 is retained in its stationary position. This push-pull action allows heart valve ring 12 to remam imbedded in the heart without danger of pushing heart valve ring 12 out of position as heart valve assembly 66 is driven therein. Once heart valve 70 has been securely positioned within heart valve ring 12, release knob 100 may be rotated to unthread threaded surface 122 of release shaft 118 from valve holder halves 68a and 68b thereby disconnecting valve assembly 66 from valve positioner 88 as shown in FIG. 23. Valve installation tool 80 is disengaged from heart valve ring 12 by breaking or cutting suture loops 132 thereby releasing hooks 112 from heart valve ring 12. Thereafter, valve installation tool 80 may be removed from the operative site.

Figure 25:
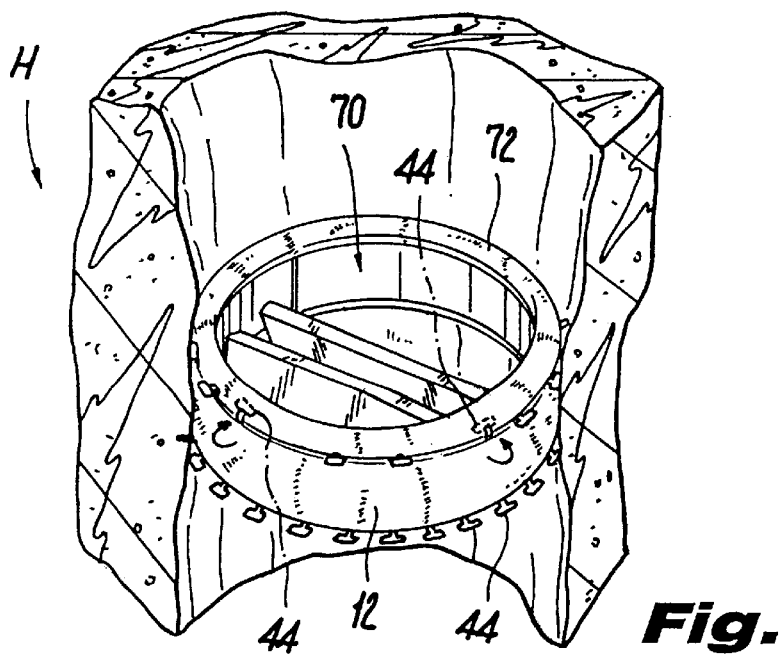
FIG. 25 is a view of the expanded heart valve ring and heart valve secured thereto within the heart tissue.

Referring now to FIG. 24, holder halves 68a and 68b may now be split apart such that flanges 76 are disengaged from ring 72 of heart valve 70. Preferably, a suture 69 is cut to release halves 68a and 68b from each other. FIG. 25 illustrates heart valve 70 positioned within heart valve ring 12 and is secured thereto by teeth 42. In order to further secure heart valve 70 to heart valve ring 12, several tabs 44 of heart valve ring 12 may be folded over ring 72 of valve 70 to thereby securely lock valve 70 to heart valve ring 12. Thus, the installation of the heart valve 70 within heart H is accomplished.

Figure 26:
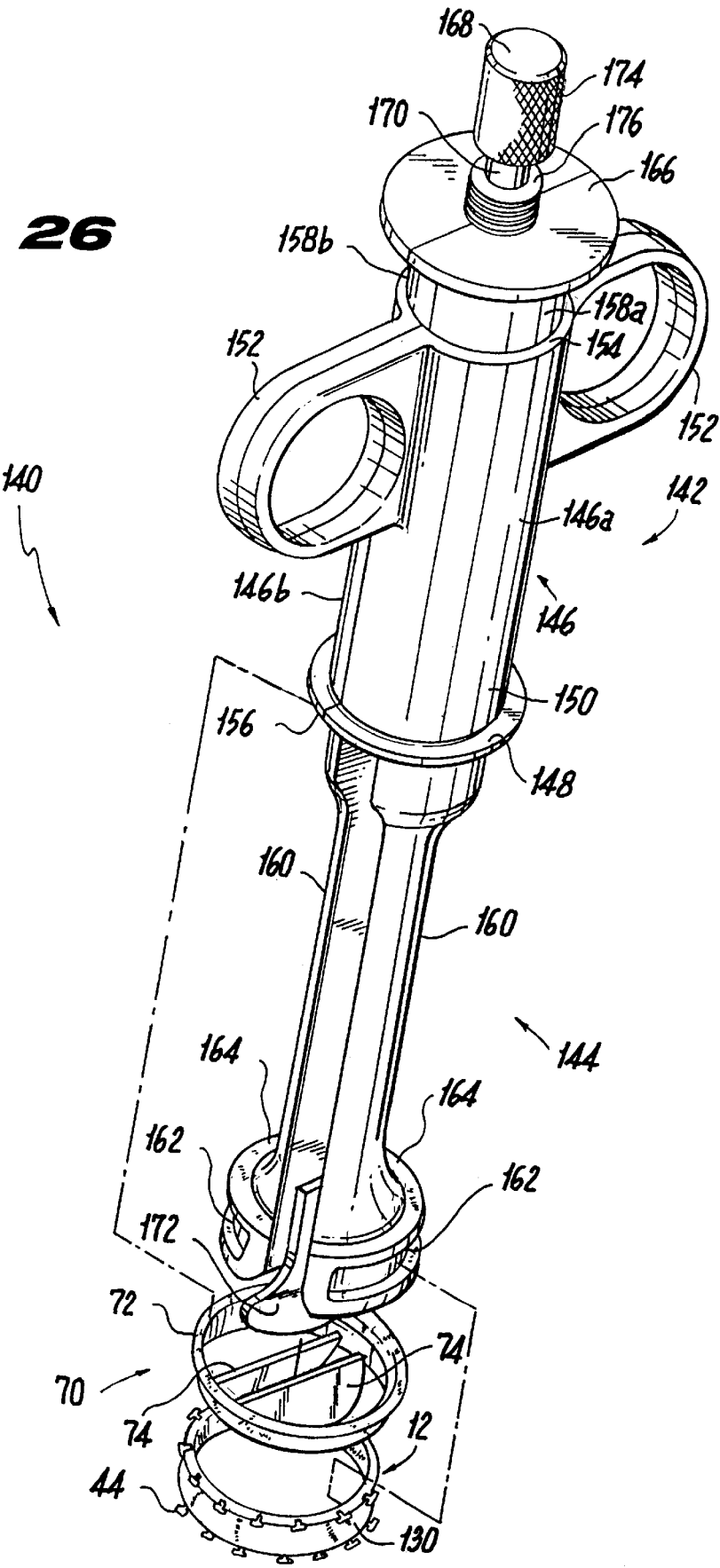
FIG. 26 is a perspective view of an alternate embodiment of a heart valve installation system including a single shot instrument for installing an expandable heart valve ring and replacement heart valve.

Referring now to FIG. 26, there is disclosed a second embodiment of a heart valve installation system having a single tool system or single shot tool 140 which is provided to install expandable ring 12, having graft material 130 therearound, into the heart and position and secure heart valve 70 within the expanded heart valve ring 12. Single shot tool 140 generally includes a valve installation assembly 142 and a ring installation assembly 144 which extends through valve installation assembly 142. Valve installation assembly 142 includes a housing 146 preferably formed as housing halves 146a, 146b. A flange 148 is provided at a distal end 150 of housing 146 and serves to hold valve 70. Finger rings 152 are provided on a proximal end 154 of housing 146. Preferably, valve 70 is retained against flange 148 by a friction surface 156. As shown in this embodiment, no additional valve holder structure is necessary.

Ring installation assembly 144 generally includes a barrel 158, preferably formed as barrel halves 158a and 158b. A pair of relatively thin flexible expander legs 160 extend distally from barrel 158. Legs 160 are approximately one-sixteenth of an inch thick. Expander legs 160 are provided with recesses 162 at a distal end 164 of each of expander legs 160. Recesses 162 are configured to securely retain expandable heart valve ring 12 when heart valve ring 12 is in a reduced diameter configuration. A flange 166 is provided at the top of barrel 158. Ring installation assembly 144 additionally includes a ring expander knob 168 having a shaft 170 extending distally therefrom. Shaft 170 extends through barrel 158. Shaft 170 cooperates with an expander blade 172 positioned on a distal end of shaft 170. Preferably, ring expander knob 168 has a knurled surface 174 to facilitate actuation thereof. A threaded collar 176 having a threaded surface 178 is affixed within barrel halves 158a and 158b and slidably and rotatably supports shaft 170.

Figure 27:
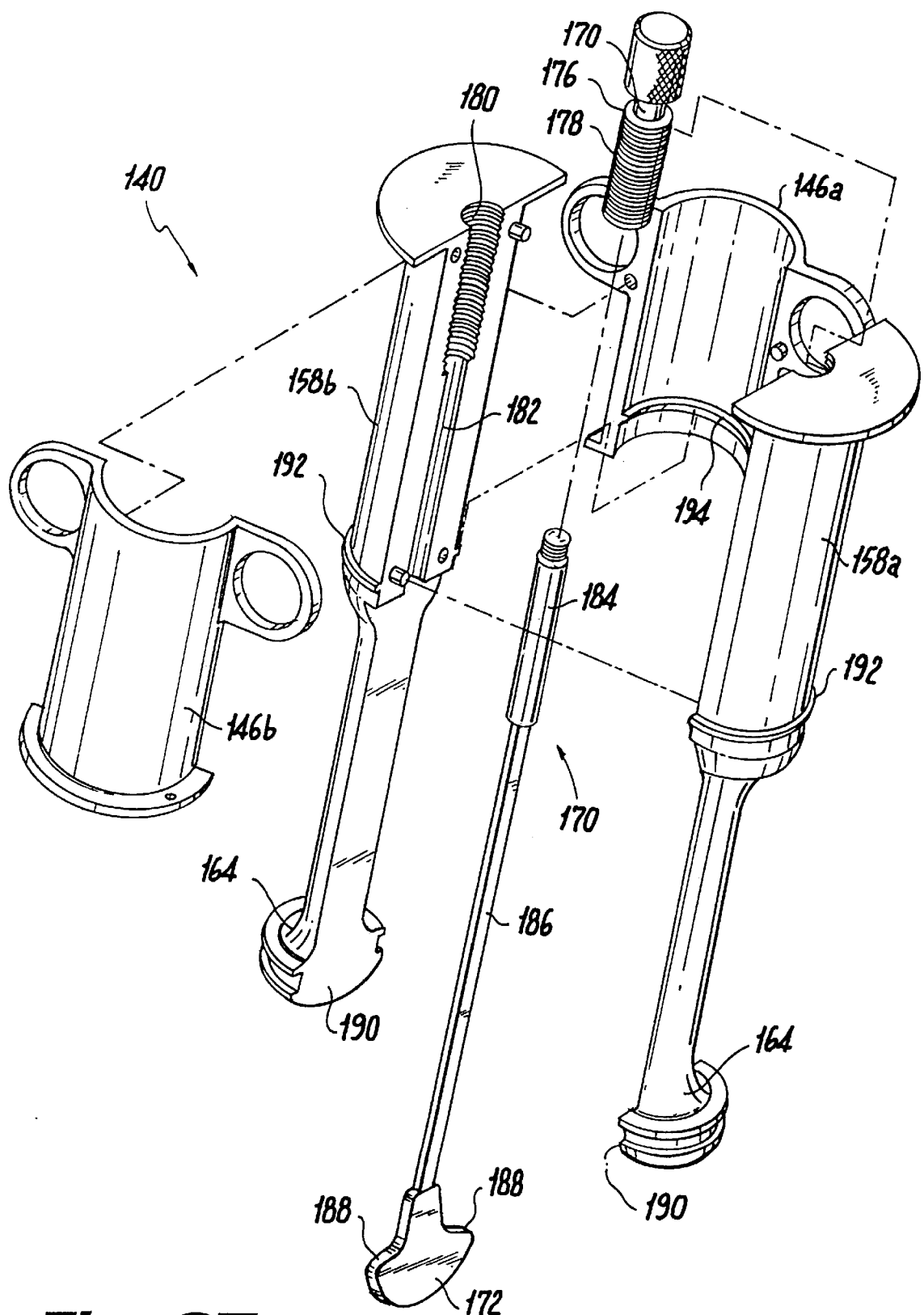
FIG. 27 is a perspective view of the single shot instrument of FIG. 26, with parts separated.

Referring now specifically to FIGS. 27 and 28, single shot tool 140 is illustrated without an artificial valve or heart valve ring installed thereon. Threaded surface 178 of collar 176 is configured to engage a threaded surface 180 which extends partially along a bore 182 formed by barrel halves 158a and 158b. Shaft 170 additionally includes a tubular portion 184 movably mounted in collar 176 and a generally rectangular portion 186 extending distally therefrom. Expander blade 172 is provided at a distal end of rectangular portion 186. Rectangular portion 186 and expander blade 172 are dimensioned and configured to fit between leaflets of a valve. In order to expand a ring held within recesses 162, expander blade 172 is provided with a pair of camming surfaces 188 which cooperate with camming edges 190 formed on distal end 164 of expander legs 160. Thus, by moving shaft 170 proximally relative to expander legs 160, camming surfaces 188 engage camming edges 190 to bias expander legs 160 apart.

In order to inhibit longitudinal movement of valve installation assembly 142 relative to ring installation assembly 144, barrel halves 158a and 158b are provided with a circumferential flange 192 which is configured to releasably engage a lip 194 formed on an inner surface of housing halves 146a and 146b.

The various motions of single shot tool 140, without an artificial heart valve or heart valve ring installed thereon, will now be described. As shown in FIG. 29, proximal movement of knob 168 draws shaft 170 and thus blade 172 proximally relative to expander legs 160. As blade 172 is drawn proximally, camming surfaces 188 engage camming edges 190 of expander legs 160 thereby spreading camming legs 160 apart. Further, distal advancement of housing 146 relative to barrel 158 causes a lip 194 to disengage from flange 192 freeing valve installation assembly 142 for relative movement relative to ring installation assembly 142.

The method of using the second embodiment of the heart valve installation system including single shot tool 140 to install an expandable heart valve ring 12 and a heart valve 70 within a heart H will now be described. Access to heart H is accomplished in a manner similar to that described hereinabove including the use of a retractor R to maintain access through the thoracic cavity to the heart (FIG. 14).

Figure 30:
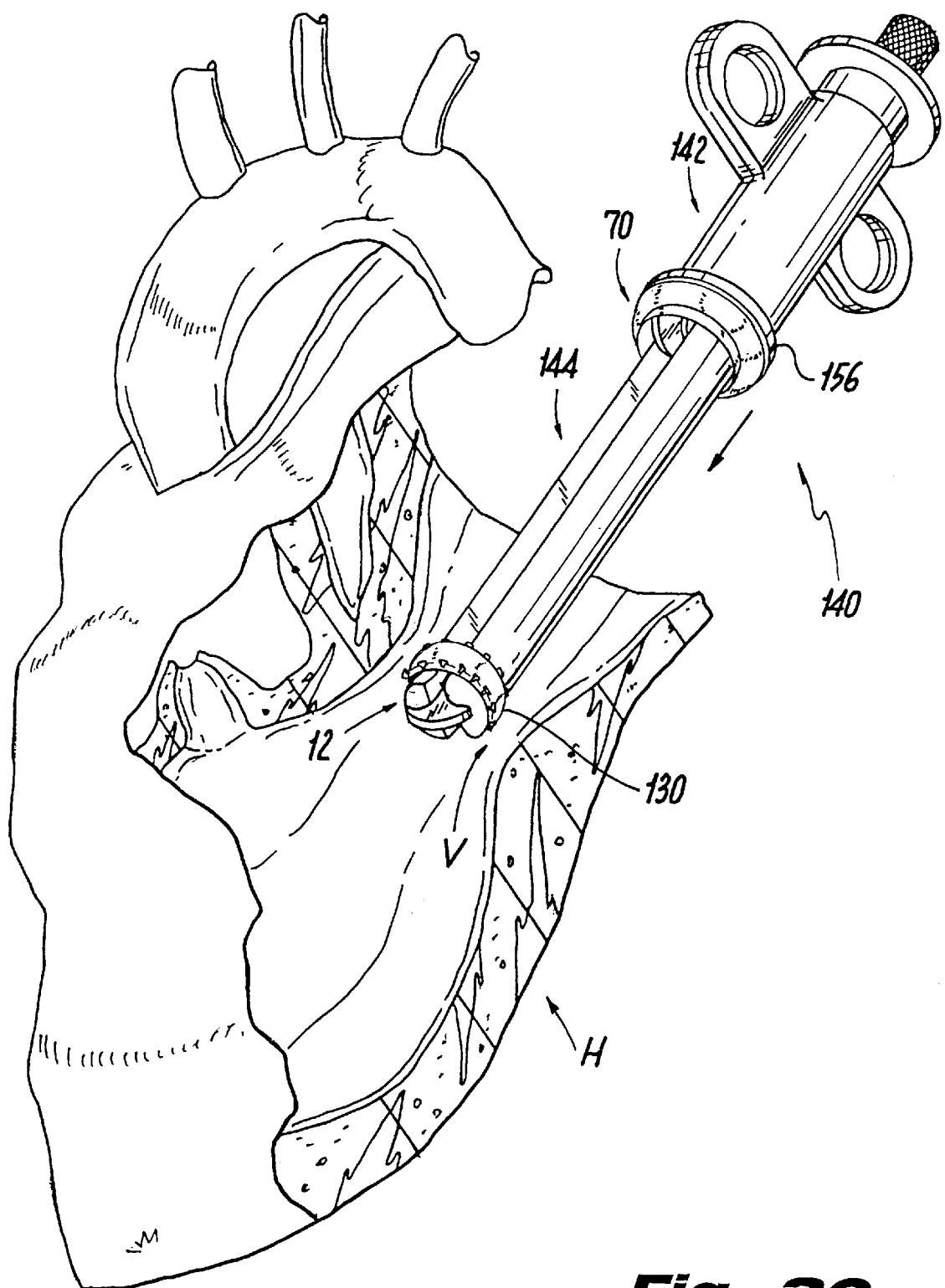
FIG. 30 is a perspective view of a heart with the natural valve removed and the single shot instrument with an expandable heart valve ring and heart valve assembled thereon and in position to be actuated.

Referring now to FIG. 30, single shot tool 140 is prepared by installing expandable heart valve ring 12, preferably with graft material 130 thereabout, on ring installation assembly 144. A synthetic replacement valve 70, is installed on valve installation assembly 142 without the use of a separate valve holder. As noted above, valve 70 may be retained on valve installation assembly 142 by means of friction surface 156.

Figures 31, 32, 33:
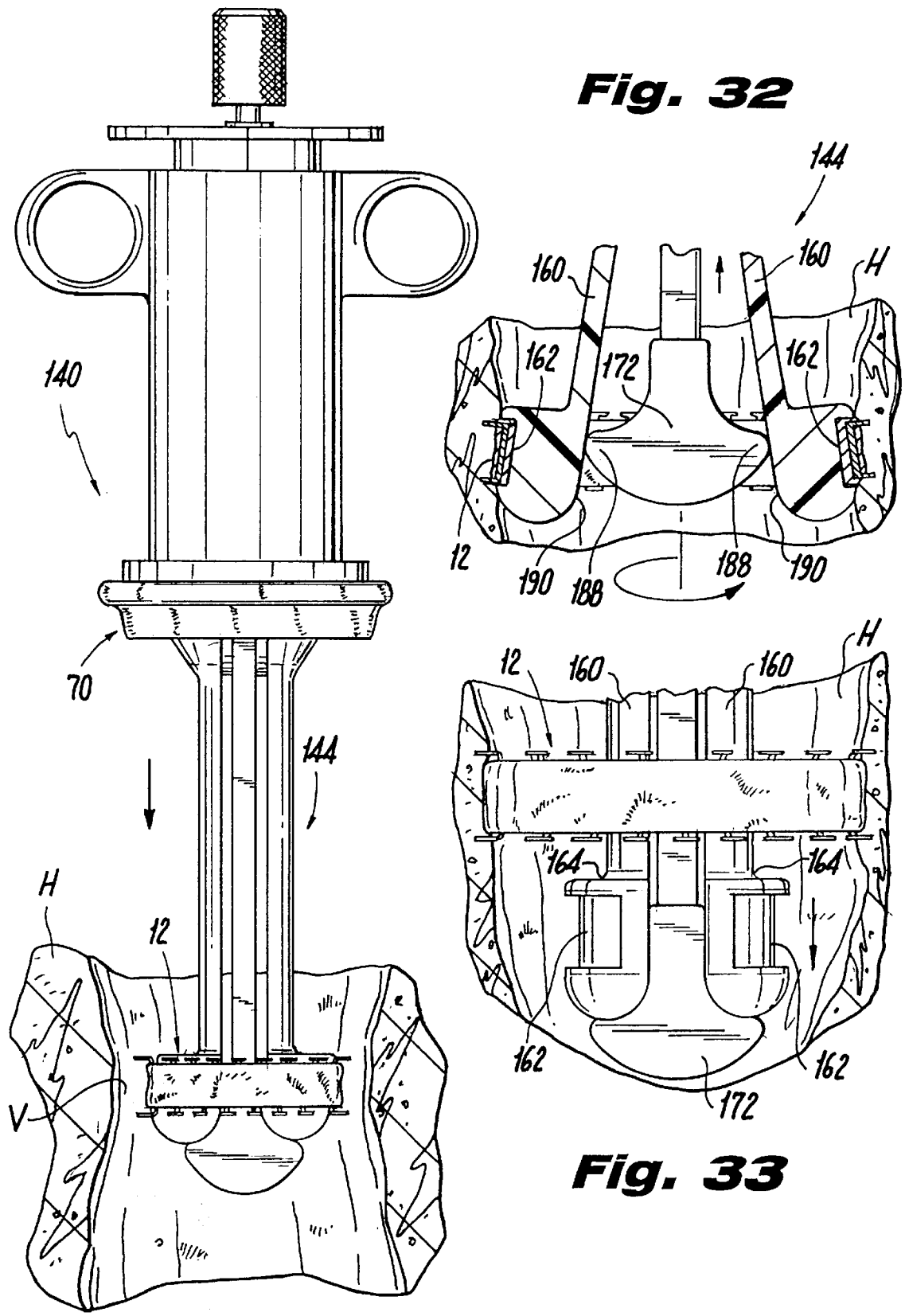
FIG. 31 is a plan view of the assembly of FIG. 30 with the distal end of the single shot instrument and expandable heart valve ring positioned at the installation location within the heart.
FIG. 32 is a view of the distal end of the ring installation assembly of the single shot instrument expanding the heart valve ring into engagement with the heart.
FIG. 33 is a view similar to FIG. 32 with the heart valve ring expanded and affixed to heart tissue and the distal end of the ring installation assembly in a collapsed condition.

As shown in FIG. 31, single shot tool 140 is advanced into heart H until expandable heart valve ring 12 is positioned at the space V where the prior natural heart valve had been removed. Ring expander assembly 144 of single shot tool 140 may now be actuated.

Referring now to FIG. 32, as ring installation assembly 144 is actuated in the manner indicated above, blade 172 is drawn proximally relative to expander legs 160. As blade 172 is drawn proximally, camming surfaces 188 engage carming edges 190 on expander legs 160 thereby driving expander legs 160 apart. As expander legs 160 are driven apart, expandable heart valve ring 12, carried within recesses 162, is forced into an expanding condition against the walls of heart H. As noted hereinabove, expandable heart valve ring 12 includes structure for retaining itself in an expanded state.

Referring to FIG. 33, once heart valve ring 12 has been expanded to securely engage the heart, blade 172 may be moved distally relative to expander legs 160 thereby allowing expander legs 160 to resume a relaxed configuration releasing expanded heart valve ring 12 from recesses 162. In preparation for actuation of valve installation assembly 142, single shot tool 140 may be moved distally relative to expanded heart valve ring 12 thereby moving distal ends 164 of expander legs 160 as well as blade 172 distally of the expanded heart valve ring 12.

Figure 34:
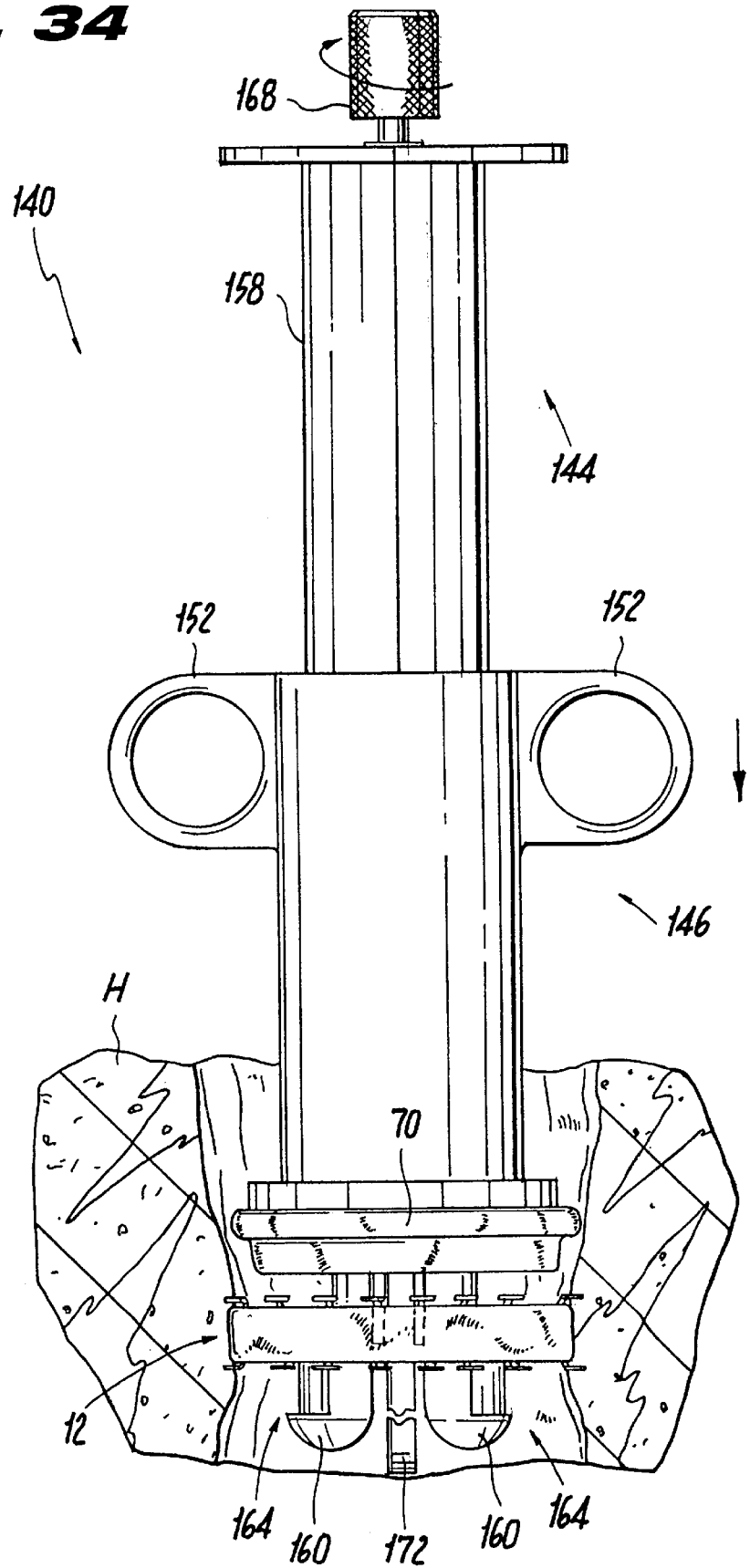
FIG. 34 is a perspective view of the single shot instrument actuating the valve installation assembly to advance the heart valve toward the expanded heart valve ring.

Referring now to FIG. 34, valve installation assembly 142 may now be moved distally relative to ring installation assembly 144. Specifically, rings 152 on housing 146 are grasped to move housing 146 distally relative to barrel 158. As shown, distal movement of valve installation assembly 142 advances heart valve 70 towards expanded heart valve ring 12.

Figure 35:
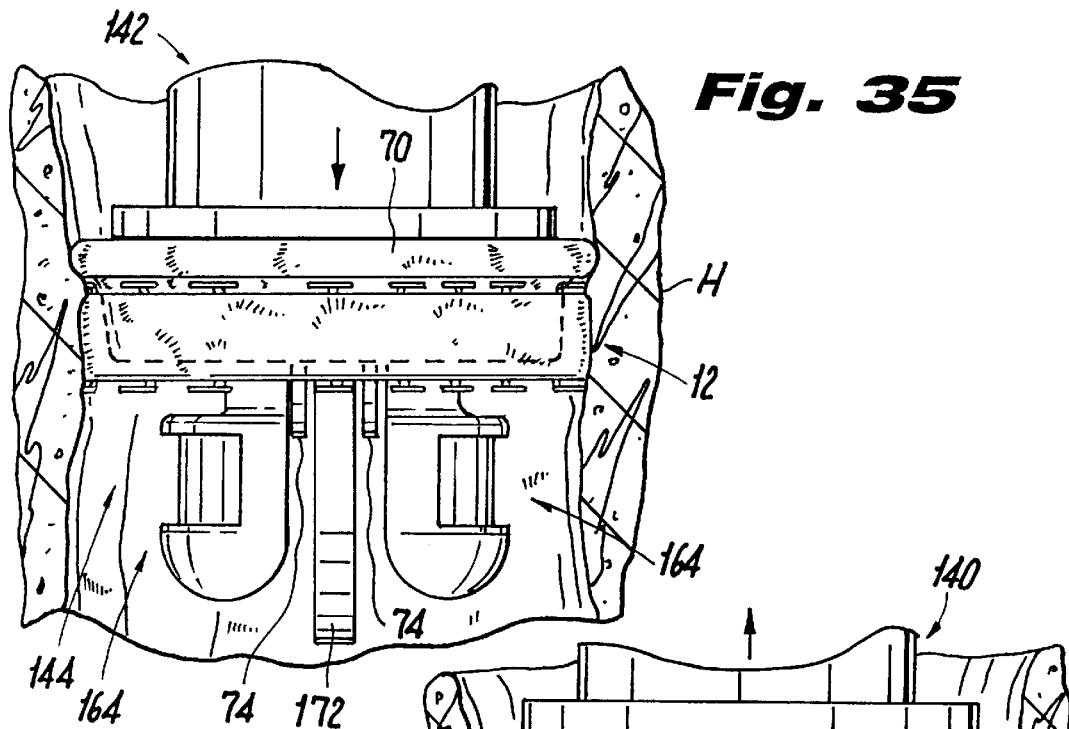
FIG. 35 is a perspective view of the heart valve positioned within the expanded heart valve ring.

Referring to FIG. 35, complete distal advancement of valve installation assembly 142 relative to ring installation assembly 144 drives heart valve 70 into engagement within expanded heart valve ring 12. Teeth 42 (not shown) engage ring 72 of heart valve 70 to secure heart valve 70 to expanded heart valve ring 12.

Figure 36:
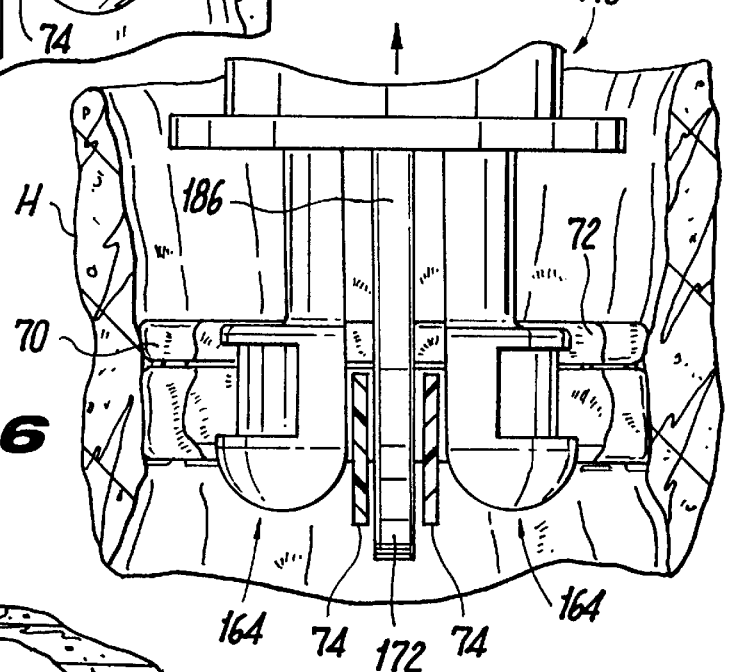
FIG. 36 is a view of the distal end of the single shot instrument being withdrawn through the heart valve.

Referring back to FIGS. 34 and 35, after distal advancement of blade 172 and expander legs 160 relative to expanded heart valve ring 12, blade 172 may be rotated approximately 90° so as to position itself between leaflets 74 of heart valve 70 (FIG. 35). Blade 172 is rotated approximately 90° relative to distal ends 164 of expander legs 160 by manipulating ring expander knob 168. As shown in FIG. 36, single shot tool 140 may now be withdrawn through heart valve 70 such that distal ends 164 of expander legs 160 pass through ring 72 and rectangular portion 186 and blade 172 pass between leaflets 74 of heart valve 70 to withdraw single shot tool 140 from the operative site.

Figure 37:
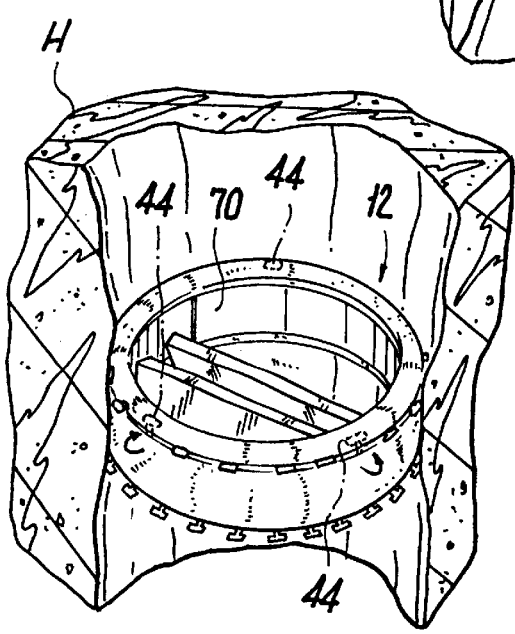
FIG. 37 is a perspective view of the heart valve being affixed to the expanded heart valve ring.

Referring to FIG. 37, heart valve 70 may be further secured to expanded heart valve ring 12 in a manner similar to that described above. Specifically, a few of tabs 44 may be folded over ring 72 of heart valve 70 to thereby secure heart valve 70 to the expanded heart valve ring 12.

It will be understood that various modifications may be made to the embodiments disclosed herein. For example, various other structure to manipulate the ring installation assemblies and valve installation assemblies relative to each other may be provided. Further, other means of securing a heart valve to the valve installation assembly and the expandable ring to the ring installation assembly are contemplated. Therefore, the above description should not be construed as limiting but merely as exemplifications of preferred embodiments. Those skilled in the art will envision other modifications within the scope and spirit of the claims appended hereto.

What is claimed is:

1. A system for installing a heart valve within a patient comprising:
    a heart valve ring implantable within the heart of a patient;
    a ring installation assembly configured to engage the heart valve ring with the heart, the ring installation assembly including a support for receipt of the heart valve ring;
    a valve installation assembly having a support to releasably support a synthetic heart valve, the valve installation assembly being operable to insert the heart valve into the heart valve ring; and
    wherein the heart valve ring includes at least one tab member foldable about the heart valve to secure the heart valve to the heart valve ring.

2. The system of claim 1, wherein the heart valve ring is expandable from a reduced diameter configuration to an increased diameter configuration to engage the heart.

3. The system of claim 2, wherein the ring installation assembly is operable to move the heart valve ring from the reduced diameter configuration to the increased diameter configuration.

4. The system of claim 2, wherein the heart valve ring is formed from an elongated strip of material and includes at least one latch which engages at least one opening formed in the strip to maintain the heart valve ring in the expanded configuration.

5. The system of claim 2, wherein the ring installation assembly has camming structure for expanding the heart valve ring from the reduced diameter configuration to the increased diameter configuration.

6. The system of claim 5, wherein movement of at least part of the camming structure distally relative to the heart valve ring moves the heart valve ring from the reduced diameter configuration to the increased diameter configuration.

7. The system of claim 5, wherein movement of at least part of the camming structure proximally relative to the heart valve ring moves the heart valve ring from the reduced diameter configuration to the increased diameter configuration.

8. The system of claim 1, wherein the ring installation assembly includes a ring installation tool and the valve installation assembly includes a valve installation tool separate from the ring installation tool.

9. The system of claim 8, wherein the valve installation tool includes a housing and a valve positioner movably associated with the housing, the valve positioner movable to insert a heart valve releasably held thereon into the heart valve ring.

10. The system of claim 9, wherein the valve installation tool includes a release mechanism to release the heart valve thereon.

11. The system of claim 9, wherein the valve installation tool includes structure for holding the heart valve ring stationary relative to at least the housing of the valve installation tool.

12. The system of claim 11, wherein the housing including distally projecting quick bars configured to engage the heart valve ring.

13. The system of claim 1, wherein the valve ring installation assembly and the heart valve installation assembly form a single instrument.

14. The system of claim 13, wherein at least a portion of the ring installation assembly is movably mounted within the heart valve installation assembly.

15. A method of installing a heart valve within a patient comprising the steps of:

providing a system including a ring installation assembly releasably supporting an expandable heart valve ring and a heart valve installation assembly releasably supporting a heart valve, the heart valve ring including at least one tab member for engagement with the heart valve;

accessing a site within the heart from which a natural heart valve has been removed;

expanding the heart valve ring into engagement with the heart;

positioning the heart valve within the heart valve ring; and securing the heart valve to the heart valve ring.

16. The method as recited in claim 15, wherein the heart valve ring is expanded into engagement with the heart tissue in response to actuation of the ring installation assembly.

17. A The method as recited in claim 15, wherein the heart valve is positioned within the heart valve ring in response to actuation of the heart valve installation assembly.

18. The method as recited in claim 17, wherein the ring installation assembly is removed from the accessed site prior to the step of actuating the heart valve installation assembly.

19. The method as recited in claim 15, wherein the heart valve ring is maintained in an expanded condition by structure incorporated into the heart valve ring.

20. The method as recited in claim 15, wherein the heart valve is positioned within the heart valve ring by engaging a portion of the heart valve installation assembly with the heart valve ring.

21. The method as recited in claim 15, wherein the heart valve is positioned within the heart valve ring by moving the heart valve installation assembly relative to the ring installation assembly.

22. The method as recited in claim 15, wherein the heart valve installation assembly is removed from the accessed site prior to the step of securing the heart valve to the heart valve ring.

23. A system for installing a heart valve within a patient comprising:

a heart valve ring implantable within the heart of a patient;

a ring installation assembly configured to engage the heart valve ring with the heart, the ring installation assembly including a support for receipt of the heart valve ring;

a valve installation assembly having a support to releasably support a synthetic valve installation, the heart valve assembly being operable to insert the heart valve within the heart valve ring, which is expandable from a reduced diameter configuration to an increased diameter configuration to engage the heart; and wherein the heart valve ring is formed from an elongated strip of material and includes at least one latch which engages at least one opening formed in the strip to maintain the heart valve ring in the expanded configuration.

* * * * *